(12) United States Patent
Ekfeldt et al.

(10) Patent No.: US 11,246,739 B2
(45) Date of Patent: Feb. 15, 2022

(54) CONVEX SHELL FOR USE IN A BASE PLATE OF AN OSTOMY APPLIANCE

(71) Applicant: Coloplast A/S, Humlebaek (DK)

(72) Inventors: Bent Ekfeldt, Copenhagen (DK); Birthe Vestbo Andersen, Espergaerde (DK); Esben Strøbech, Hoersholm (DK); Michael Hansen, Gilleleje (DK); Kristoffer Hansen, Maaloev (DK); Steffen Kongensbjerg Larsen, København (DK); Matthew Laws, London (GB); Liam O'Brien, London (GB)

(73) Assignee: Coloplast A/S, Humlebaek (DK)

( * ) Notice: Subject to any disclaimer, the term of this patent is extended or adjusted under 35 U.S.C. 154(b) by 922 days.

(21) Appl. No.: 15/976,867

(22) Filed: May 11, 2018

(65) Prior Publication Data

US 2018/0325718 A1    Nov. 15, 2018

Related U.S. Application Data

(63) Continuation of application No. 13/993,078, filed as application No. PCT/DK2011/050492 on Dec. 16, 2011, now Pat. No. 9,999,537.

(30) Foreign Application Priority Data

Dec. 17, 2010  (DK) .......................... PA 2010 70553
Dec. 17, 2010  (DK) .......................... PA 2010 70554
(Continued)

(51) Int. Cl.
*A61F 5/443*    (2006.01)
*A61F 5/445*    (2006.01)
(Continued)

(52) U.S. Cl.
CPC .............. *A61F 5/443* (2013.01); *A61F 5/445* (2013.01); *A61F 2005/4483* (2013.01)

(58) Field of Classification Search
CPC combination set(s) only.
See application file for complete search history.

(56) References Cited

U.S. PATENT DOCUMENTS 4,219,023 A * 8/1980 Galindo .................. A61F 5/445
                                                              604/344
4,710,182 A * 12/1987 Bryson ................... A61F 5/445
                                                              604/339
(Continued)

FOREIGN PATENT DOCUMENTS

EP     0806210 A2    11/1997
EP     1348412 A1    10/2003
(Continued)

OTHER PUBLICATIONS

B. Mills, "Validation of Coloplast Patent EP2 651 B1", report No. 16049, Sep. 26, 2016, p. 1.
(Continued)

*Primary Examiner* — Guy K Townsend
(74) *Attorney, Agent, or Firm* — Coloplast Corp., Coloplast A/S; Nick Baumann

(57) ABSTRACT

A convex shell for use in a base plate of an ostomy appliance includes an annular ring with a through-going hole and a plurality of grooves extending transversely across the annular ring. The grooves alter the flexibility of the annular ring as a first portion of the annular ring is folded around a folding axis toward a second portion of the annular ring.

20 Claims, 16 Drawing Sheets

(30) Foreign Application Priority Data

Dec. 17, 2010 (DK) ............................ PA 2010 70555
Dec. 17, 2010 (DK) ............................ PA 2010 70556
Sep. 9, 2011 (DK) ............................ PA 2011 70498

(51) Int. Cl.

*A61F 5/44* (2006.01)
*A61F 5/448* (2006.01)

(56) References Cited

U.S. PATENT DOCUMENTS

| | | | |
|---|---|---|---|
| 4,834,731 A * | 5/1989 | Nowak | A61F 5/448 604/339 |
| 4,846,820 A * | 7/1989 | Jensen | A61F 5/445 604/339 |
| 4,973,323 A * | 11/1990 | Kaczmarek | A61F 5/448 604/339 |
| 5,125,917 A * | 6/1992 | Whealin | A61F 5/448 604/332 |
| 5,501,678 A * | 3/1996 | Olsen | A61F 5/443 604/344 |
| 5,607,413 A * | 3/1997 | Holmberg | A61F 5/448 604/332 |
| 5,718,696 A * | 2/1998 | Kollerup | A61F 5/443 604/339 |
| 5,730,735 A * | 3/1998 | Holmberg | A61F 5/448 604/338 |
| 6,589,222 B1 * | 7/2003 | Olsen | A61F 5/443 604/336 |
| 6,673,056 B2 * | 1/2004 | Metz | A61F 5/448 604/332 |
| 8,684,983 B2 * | 4/2014 | Andersen | A61F 5/445 604/338 |
| 2002/0088080 A1 * | 7/2002 | Fenton | A61F 5/445 15/389 |
| 2004/0193123 A1 * | 9/2004 | Fenton | A61F 5/448 604/344 |
| 2005/0054997 A1 * | 3/2005 | Buglino | A61F 5/443 604/332 |
| 2011/0218507 A1 * | 9/2011 | Andersen | A61F 5/445 604/338 |
| 2014/0316360 A1 * | 10/2014 | Ekfeldt | A61F 5/445 604/344 |

FOREIGN PATENT DOCUMENTS

| | | |
|---|---|---|
| EP | 2651351 A1 | 6/2012 |
| JP | 11290364 A2 | 10/1999 |
| WO | 9300056 A1 | 1/1993 |
| WO | 2004087004 A2 | 10/2004 |
| WO | 2009021517 A1 | 2/2009 |

OTHER PUBLICATIONS

Photos of ostomy base plate from Marlen Manufacturing and development company.
Photos of ostomy base plate from Pelican Healthcare Limited.
Instructions for use, dated Nov. 2010.
Produktguide Kristine Hardam A/S, dated Sep. 2008.
Notice of opposition against EP3175830, dated Mar. 30, 2021.

* cited by examiner

CONVEX SHELL FOR USE IN A BASE PLATE OF AN OSTOMY APPLIANCE

FIELD OF THE INVENTION

The present invention relates to a base plate for an ostomy appliance. In particular, the present invention relates to a base plate comprising an adhesive wafer to which a convex supporting device is secured. The present invention further relates to a convex supporting device for a base plate of an ostomy appliance. Moreover, the present invention relates to an ostomy appliance comprising a base plate with a convex supporting device and a collecting bag.

BACKGROUND

Base plates are used in ostomy appliances to attach ostomy bags to the skin of a user having a stoma, the user also being referred to as an ostomate or ostomist.

The base plate is typically formed by a backing layer, e.g. a polyurethane film, on which a skin friendly adhesive is disposed. A through-going passage is arranged in the base plate to receive a stoma so that the base plate may be adhered to the skin surrounding the stoma.

In order to collect output from the stoma, the opening of an ostomy bag is arranged around the through-going passage. The ostomy bag may, for example, be arranged by welding the bag to the backing layer of the base plate. In the art, this is referred to as a one-piece ostomy appliance. Alternatively, a coupling arrangement, either adhesive or mechanical, may be arranged so that ostomy bags may be arranged detachably on the base plate. This allows the bag to be changed when full without detaching the base plate from the skin. In the art, this is referred to as a two-piece ostomy appliance.

A number of ostomates develop sunken or retracted stomas. This is a phenomenon where the stoma sinks into the abdomen creating a recess or cavity in the stomach where the stoma is placed. Applying a standard planar base plate around such a retracted stoma would, for one thing, leave the peristomal skin area immediately around the stoma uncovered and thereby exposed to the output from the stoma. Moreover, in some cases, the stoma is retracted so much that it is not even possible for it to extend or protrude through the through-going passage in the base plate. This means that the risk of leakage is increased. By leakage is meant that the stomal output containing aggressive, enzymatic fluids, enters underneath the adhesive of the base plate and leading to adhesion failure. In order to address the issue of retracted stomas, and the consequently encountered frequent leakage problems, convex base plates have been developed.

Basically, these have a convex surface contour where an outer planar area is adhered to an outer skin area which surrounds the stoma, but where the skin is not pulled inwards towards the stoma. An intermediate area of the convex surface, having a slanting surface along the axis of the through-going passage, adheres to the skin area between the outer skin area and the inner skin area described hereafter. Finally, an inner planar area of the convex surface is adhered to an inner skin area immediately surrounding the stoma.

Such products have been available on the markets for many years. Their primary purposes and advantages are that they are able to prevent the peristomal skin of the ostomist's body from collapsing on to the stoma and practically closing off the stoma, e.g. due to excess skin folds caused by overweight or obesity. Such collapse potentially causes a dislodgement of the product from the body. Another purpose of the convex products is to increase the ability of the stoma to protrude adequately past the interface between the base plate and the body surface by maintaining a necessary pressure in the peristomal skin area, thus making sure that the stomal output deposits directly into the collecting bag.

Generally, however, these products are relatively stiff and inflexible and will not follow the ostomist's body movements caused by physical activity very well. More severely, experience has shown that the use of these products may in some cases result in peristomal skin damage such as pressure wound ulceration and bruises.

In more recent years, an increased variety of convex base plate products have been made available to ostomists. Particularly, if the recess or cavity in the body may be relatively shallow, i.e. when the stoma is only retracted to a lesser degree, a less bulky and less stiff convex base plate may be appropriate. Furthermore, there has been a desire to alleviate at least some of the user-experienced discomfort caused by the stiffness and inflexibility of the known stiff convex base plates. To overcome these and other needs, what is commonly accepted as "soft convex base plates" have been developed. These have a higher degree of flexibility than the stiff convex base plates and thus improve user comfort. These products may or may not comprise an injection moulded convex element.

However, the increased flexibility and comfort of the "soft convex base plates" products have compromised their ability to maintain the necessary pressure on the peristomal skin area to keep the stoma adequately protruding.

Thus, there is an unmet need to improve convex base plates so as to provide products that can maintain a relatively constant and adequate pressure in the peristomal skin area without simultaneously compromising the improved flexibility experiences with the soft convex base plates.

SUMMARY OF THE INVENTION

With the present invention, products with an optimal balance between the values of the bending resistance and the axial compression resistance of convex ostomy devices have been achieved. Up until now, it has not been possible for users to find a product in this optimal balance range, because available devices were either too rigid or too soft. The product types according to the invention offer a comfortable level of bending resistance and security against peristomal collapse, while also maintaining the necessary peristomal pressure without the risk of pressure ulcers occurring.

DETAILED DESCRIPTION OF THE INVENTION

In a FIRST aspect, the present invention relates to a base plate for an ostomy appliance comprising a skin friendly adhesive with a first through-going passage for receiving a stoma, the passage surrounded by a first adhesive area protruding from and surrounded by a second adhesive area, wherein the first adhesive area protrudes at least 7 mm from the second adhesive area; and wherein the axial compression resistance to moving the first adhesive area towards the second adhesive area axially along the centre axis of the through-going passage is above 10 Newton at 3 mm compression; and wherein the bending resistance of the base plate about a horizontally extending bending axis perpendicular to the centre axis of the first through-going passage is below 2.25 Newton at 20 mm bending.

It will be appreciated that by providing a base plate which has high axial compression resistance, the base plate will have an improved ability to maintain its convex shape when it is attached to the skin of the user. Thus, in cases where the stoma is provided in a cavity of the skin of the user, the likelihood of the base plate disconnecting from the skin in the aforementioned cavity is reduced. It will be appreciated that this reduces the risk of faecal matter flowing in-between the base plate and the skin of the user, whereby the risk of leakage and irritation of the skin of the user is reduced or even eliminated, because of the ability to maintain the necessary peristomal pressure.

Moreover it will be appreciated, that by providing a base plate which may easily be bent, the base plate will be more comfortable to wear than conventional base plates. The reason for this is that it will be easier for a user to bend the upper body towards the legs (which will result in the skin of the stomach being contracted or skin folds of the stomach being compressed). In other words, when the reaction force of a convex base plate is below level of 2.25 N when exposed to bending, it means that the convex base plate is more flexible and thus more comfortable.

Based on our findings confirmed during interviews with users and healthcare professionals it has been found that this is indeed an optimal balance range between the values of the bending resistance and the axial compression resistance of convex ostomy devices. Up until now, is has not been possible for users to find a product in this optimal balance range because devices were either too rigid or too soft. With products according to the invention this may now be possible.

Prior art devices rely on a mechanism where a fairly stiff plate levels out the skin and skin folds around the stoma and therefore need a fairly hard axial force to get the skin immediately surrounding the stoma pressed inwards so the stoma will get through the base. The present invention bends into skin folds (due to the low bending resistance) easing the requirement for structured convex stiffness.

The invention ensures that the base plate has a superior fit to the peristomal contours of users with concave peristomal areas due to its construction that creates the necessary pressure to the peristomal area while being flexible, particularly in the horizontal direction, which ensures an increased freedom of movement and mobility of the user. Moreover, a more secure seal to the user's skin than with available standard care products is achieved and results in a reduced degree of leakage under the base plate.

In the context of this application, horizontal direction means a direction being substantially parallel to a user's waistline when the product is attached to a user's body around a stoma.

It is our experience with this type of products that the adhesive force needed to keep the base plate attached to the skin can be lowered. As the base plate does not work against the natural movements and foldings of the skin, but due to the flexibility work with the natural movements and folding of the skin, the adhesive force, i.e. the adhesive strength, can be less. Thus, it is easier to remove the base plate, and the skin is not irritated with every change of base plate. Thus, users experience a reduction in the frequency of problem related product changes.

In a preferred embodiment, the axial compression resistance is less than 40 N. Hereby, the risk of creating pressure marks or ulcers compared to standard convex products is reduced, while the ability to keep the stoma within the base plate and thereby preventing leakage is maintained.

The through-going passage in the base plate may be arranged substantially in the centre of the adhesive wafer and be adapted to receive a stoma of the user. However, in some embodiments, an inner circumference defined by the inner edge of the through-going hole may be eccentrically arranged with respect to an outer circumference defined by the outer edge of the base plate.

In embodiments, the base plate further comprises a convex supporting device. Such convex base plates are manufactured by pressing a planar base plate together with a convex supporting device e.g. in the shape of a convex shell. Such a convex supporting device may be manufactured by an injection moulding process. The convex shell has the desired contour and shape and is formed in a material which is more rigid than the planar base plate. The planar base plate is pressed to the shape of the convex shell, then they are joined together, typically by welding or an adhesive. This can also be done by vacuum-forming.

In embodiments, the convex supporting device comprises a second through-going passage. The second through-going passage may be aligned with the first through-going passage of the base plate to receive a stoma of a user.

In embodiments, the convex supporting device is attached in a first attachment zone. Typically, such first attachment zone is within the first adhesive area.

In embodiments, the convex supporting device is attached in a second attachment zone. Typically, such second attachment zone is within the second adhesive area. Preferably, however, if the supporting device is attached in the second attachment zone it is also attached in the first attachment zone.

In embodiments, the second attachment zone encircles the first attachment zone.

In some embodiments referred to above, the convex supporting device is attached to the base plate in a first attachment zone. This first attachment zone may be circular and co-axial with the centre axis of the through-going passage of the base plate. In some embodiments, the convex supporting device is also attached to the base plate in a second attachment zone which encircles the first attachment zone. Like the first attachment zone, the second attachment zone may be circular and the two zones may be co-axial. The convex supporting device may be attached to the distal side of the base plate, e.g. to the backing layer. In some embodiments, the convex supporting device is not secured to the base plate in an area or space defined between the first and the second attachment zones, while in other embodiments it may be further secured in said area or space, e.g. by means of adhesive.

In embodiments, the convex supporting device is embedded. It may be embedded fully in the adhesive material or between the adhesive and the backing layer of the base plate. In this case a first attachment zone may be one or more areas on one or both sides of the convex supporting device. That or those area(s) may constitute a percentage of the total adhesive surface area of the first and second adhesive areas. Thereby, the securing of the convex supporting device can be achieved without the need for welding and/or adhesive attachments.

Depending on the degree and/or position(s) of attachment of the convex supporting device to the base plate, the bending and axial compression resistance of the base plate may be influenced. Particularly with regard to the bending resistance, it is understood that if the convex supporting device is attached in two attachment zones, it will be more resistant to bending than if it is only attached in one attachment zone. Similarly, if the convex supporting device is attached over most or all of its surface, it will be more resistant to bending than if only attached over a smaller percentage of its surface. Furthermore, the same goes for the position of attachment. If the convex supporting device is attached to the base plate relatively far from the through-going passage thereof, it will be more resistant to bending than if attached close to the passage.

In embodiments of the invention, it is ensured that a convex supporting device can be attached to the base plate relatively far from the through-going passage while still showing a very low bending resistance, making the products of the invention highly flexible and thus comfortable to wear, see e.g. FIGS. 9 and 12.

In embodiments, the supporting device may define a first and a second bending axis both of which define a right angle with the centre axis of the through-going passage. Moreover, the first and the second bending axis may define a right angle with respect to each other, while in other embodiments the bending axes are not at a right angle to each other. In one embodiment, the bending resistance when bending the base plate about the first and the second bending axes is identical. Alternatively, the bending resistance is higher when bending the base plate about the second axis than when bending the base plate about the first axis. In use, the base plate may be adapted to be orientated such that the first bending axis extends generally in the horizontal direction.

In one embodiment, the bending resistance may be determined by bending the base plate a predetermined bending distance about the respective bending axis. The predetermined bending distance may be 5 mm, or 10 mm, or 15 mm, or 20 mm, or 25 mm, or 30 mm, or 35 mm, or 40 mm, or 45 mm or 50 mm. Alternatively, the predetermined bending distance constitutes a predetermined percentage of the diameter of the base plate or of the convex supporting device, such as 10 percent, such as 15 percent, such as 20 percent, such as 25 percent, such as 30 percent, such as 35 percent, such as 40 percent or such as 50 percent; the predetermined percentage may be in the range 10 to 50 percent, such as 20 to 40 percent or such as 22 to 36 percent.

The bending resistance may be measured as the reaction force of the base plate acting on the tool used to bend the base plate, when the base plate has been bent the predetermined bending distance or percentage. Alternatively, the bending resistance may be the maximum resistance which the base plate exerts on the tool during bending from the unbent state to the bent stage. Accordingly, the bending resistance may be the resistance exerted on the tool prior to the base plate being bent into the predetermined bending distance or percentage.

In embodiments, the bending resistance is below 2 Newton at 20 mm bending about the horizontal bending axis.

In embodiments, the bending resistance is below 1 Newton at 20 mm bending about the horizontal bending axis.

In an embodiment, the bendability resistance is above 0.5 N to avoid collapse of the peristomal skin area.

In embodiments, the convex supporting device is designed such that the bending resistance of the base plate is below one of the previously mentioned bending resistance levels, such as below 2 Newton, when the base plate is bent 20 mm about the bending axis from an initial unbent position to a bent position.

The bending resistance is determined by mounting the base plate in a tool comprising two opposite tool members which are forced towards each other during the bending test, whereby the base plate is bent. The distance between the two opposing tool members prior to the testing action is set to a distance corresponding to the diameter of the convex supporting device prior to initiating the test. Thus, any part of the base plate which extends further away from the centre axis of the base plate than the rim (outer periphery) of the convex supporting member may be folded prior to the base plate being secured in the test device. Once the base plate has been positioned between the two opposite tool members, the two tool members may be moved towards each other in order to determine the bending resistance.

An axial compression resistance of the improved base plate may be determined by compressing the base plate in a direction parallel to the centre axis of the through-going passage. By compressing the base plate is meant incurring a compression force to the base plate. Like in the case of the bending resistance, the axial compression resistance may, in one embodiment, be the resistance measured once the base plate has been compressed the predetermined axial distance, while in other embodiments, the axial compression resistance is the maximum axial resistance which has been measured during the axial compression of the base plate from the uncompressed state to the compressed state.

In one embodiment, the base plate is compressed a predetermined axial distance, which may be 1 mm, or 2 mm, or 3 mm, or 4 mm, or 5 mm, or 6 mm. Alternatively, the predetermined axial distance may constitute a predetermined percentage of the largest axial dimension of the base plate or of the convex supporting device, such as 5 percent, or 10 percent, or 15 percent, or 20 percent, or 25 percent, or 30 percent, or 35 percent, or 40 percent, or 45 percent or 50 percent.

In embodiments, the axial compression resistance may be 10 Newton, or 15 Newton, or 20 Newton, or 25 Newton, or 30 Newton, or 35 Newton, or 40 Newton, or 45 Newton, or 50 Newton or 60 Newton.

The axial compression resistance may be determined by applying an axial pressure to the base plate such that the first attachment zone or first adhesive area and the second attachment zone or second adhesive area are moved/compressed towards each other in a direction parallel to the centre axis. In other words, one or both of the zones or areas is/are pushed towards the other. It is to be understood that the axial pressure is applied in such a way that the entire or whole first and/or second adhesive area or zone is moved along the centre axis. As an example, the force may be applied to predetermined positions of the base plate. In one embodiment, the force is applied to the two points/zones which, in the direction of the centre axis of the through-going passage, are farthest away from each other. In another embodiment, the axial pressure is applied to the first and the second zones, in which the convex supporting device is secured to the adhesive wafer. Means may be provided to retain the test specimen so that it does not move in the transverse direction when exerted to the compression force.

In embodiments of the invention, the base plate has a bending resistance below 2.25 Newton at 20 mm bending and an axial compression resistance at 3 mm compression of 5-40 times the value of the maximum bending resistance measured in Newton.

In the context of the application, the meaning of the word protrude or protruding (or other variants thereof) is to be understood as a protruding element being "further forward" than the rest of something. When it is mentioned that a stoma is protruding it therefore means that the stoma opening (in the first adhesive area) is in a position where it touches the skin first, that is, it is more proximal to the skin of the user than the remainder of the base plate (the second adhesive zone). When it is mentioned that a first adhesive area is protruding from a second adhesive area it is to be understood that at least a part of the first adhesive area lies in a plane substantially parallel to the plane of the second adhesive area and displaced a distance along an axis perpendicular to those planes. With a base plate according to the invention it means that the first adhesive area is closer to the skin than the second adhesive area when observed before the product is actually mounted on the skin. Hereby, a convex device is formed.

In an embodiment, the invention relates to a base plate for an ostomy appliance, the base plate comprising an adhesive wafer for adhering the base plate to a skin area of a user, the adhesive wafer defining a through-going passage for receiving a stoma of a user, wherein the base plate comprises a convex supporting device which is secured to the adhesive wafer in a first zone, wherein the convex supporting device is designed such that a bending resistance of the base plate about a bending axis which is perpendicular to a centre axis of the through-going passage is below a first predetermined level, and such that an axial compression resistance of the base plate in a direction parallel to the centre axis is above a second predetermined level.

It is preferred, that the first predetermined level is 2 Newton per 20 mm, and the second predetermined level is 10 Newton per 3 mm.

In an embodiment, the convex supporting device is designed such that the bending resistance of the base plate is below 2 Newton, when the base plate is bent 20 mm about the bending axis from an initial unbent position to a bend position.

In an embodiment, the convex supporting device is designed such that the axial compression resistance of the base plate is at least 10 Newton, when the base plate is compressed 3 mm in an axial direction from an initial uncompressed position to a compressed position.

In another embodiment of the invention, the plate comprises a vacuum-heat shaped convex backing layer made from a suitable thermoplastic material such as, but not limited to, polypropylene, polyethylene or polyurethane or combinations thereof.

In the field of ostomy appliances, a base plate is usually defined as an entity basically consisting of two primary components. The first component is a backing layer (also referred to a s a top film), one surface of which functions as a carrier layer for a skin friendly adhesive and the other surface functions as a base for attachment of a collecting bag. The backing layer may be permeable, impermeable or semi-permeable to moisture. The second component is the adhesive layer of a skin-friendly adhesive, at least the part of the adhesive that is in touch with the skin should be skin-friendly. The base plate may further comprise other elements, e.g. one or more release liners to be removed before application of the adhesive surface to the skin.

Common materials used for backing layers include polyethylenes and polyurethanes. Common materials for release liners include polypropylene or polyethylene terephthalate.

With regard to the skin friendly adhesive, pressure sensitive adhesives have for a long time been used for attaching medical devices, such as ostomy appliances to the skin.

Due to the delicate nature of skin, there is a narrow window where a pressure sensitive adhesive can function as a good and skin friendly adhesive: On one hand, the adhesive should be able to attach the medical device to the skin and the device should not fall of during wear and on the other hand, removal of the medical device from the skin should not cause damage to the skin (known as skin cell stripping).

Some examples of different kinds of pressure sensitive adhesives that may be used for the adhesive of the base plate of the present invention are introduced below. The examples do not represent an exhaustive list.

Hydrocolloid adhesives containing hydrophilic particles or absorbents, which absorb moisture into the adhesive bulk and transmit moisture when conditions are saturated, are one well-known group of pressure sensitive adhesives useful for attaching medical devices to the skin.

Pressure sensitive adhesives based on polymers like SIS and PIB are well known in the technical field of ostomy appliances. A couple of examples may be seen in WO 99/11302 describing adhesives for medical use based on SIS, PIB and hydrocolloids and U.S. Pat. No. 4,551,490 describing adhesives containing SIS/SI, PI B/butyl rubber, tackifier, mineral oil and hydrocolloids.

Another kind of pressure sensitive adhesive suitable for the base plate of the present invention is based on polymers that may generally be copolymers of ethylene and a polar monomer. The copolymers typically comprise less than about 70% ethylene, have water vapour transmission of more than 50 $g/m^2/day$ and a melt flow index of less than 2 g/10 min (190° C./21.1 N). The melt flow index can be measured by the methods given in ISO 1133 and ASTM D1238. Examples of such polymers are copolymers of ethylene and vinyl acetate and copolymers of ethylene and butyl acrylate. Particularly preferred is ethylene and vinyl acetate copolymers with more than about 40% (w/w) vinyl acetate, a melt flow index of less than 2 g/10 min (190° C./21.1 N), and a water vapour transmission of more than 50 $g/m^2/day$ for a 150 μm sheet when measured according to MVTR Test Method.

The polar monomer may be a polar oil, generally those that have good solubility in the polar domains of the polymer, i.e. provide softness without sacrificing too much tensile strength of the polymer. Preferred polar oils are esters, ethers and glycols, and particularly preferred is Poly Propylene Oxide, e.g. alpha-butoxy-polyoxypropylene.

In a SECOND aspect, the present invention relates to an ostomy appliance comprising a base plate as discussed herein and a collecting bag.

In embodiments of the second aspect, the collecting bag is detachably attached to the base plate, thereby forming a two-piece ostomy appliance.

In embodiments of the second aspect, the collecting bag is permanently attached to the base plate, thereby forming a one-piece ostomy appliance.

It will be appreciated that the ostomy appliance according to the second aspect may comprise any combination of features and/or elements of the invention according to the first aspect.

A THIRD aspect the present invention relates to a convex supporting device for a base plate of an ostomy appliance, the device having a through-going passage and wherein the device has a bending resistance about a horizontally extending bending axis, which is perpendicular to a centre axis of the through-going passage, which is below 2.25 Newton at 20 mm bending and an axial compression resistance in a direction parallel to the centre axis above 10 Newton at 3 mm compression.

The convex supporting device may be used with regular base plates (i.e. "flat" or planar plates) to achieve a convex product with the same benefits as described with respect to the first aspect of the invention. Moreover, the convex supporting element may be connected or attached to the base plate in a similar manner and/or in similar positions as described with respect to the first aspect. Alternatively, the convex supporting device of the third aspect of the invention may be provided with attachment means on some or all of its surfaces, e.g. in the form of an adhesive covered by one or more release liners that is/are removed before application, such that the convex supporting device may be attached to a regular base plate. Thereby, even users not being in possession of a convex ostomy appliance may apply the convex supporting device to their standard product and enjoy the benefits described.

BRIEF DESCRIPTION OF THE DRAWING

The invention will now be described in detail with reference to the figures in which FIG. 1 discloses a cross-sectional view of the base plate according to the present invention, FIGS. 2 and 3 disclose cross-sectional view of the base plate when attached to the skin of a user, FIG. 4 discloses a testing device for determining the axial compression resistance of a base plate, FIG. 5 discloses bending of a base plate, FIGS. 6 and 7 disclose provision of a base plate in a bending resistance testing device, and FIG. 8 discloses a graph illustrating the combination of bending resistance and axial compression resistance of various embodiments of the invention.

DETAILED DESCRIPTION OF THE DRAWING

Figure 1:
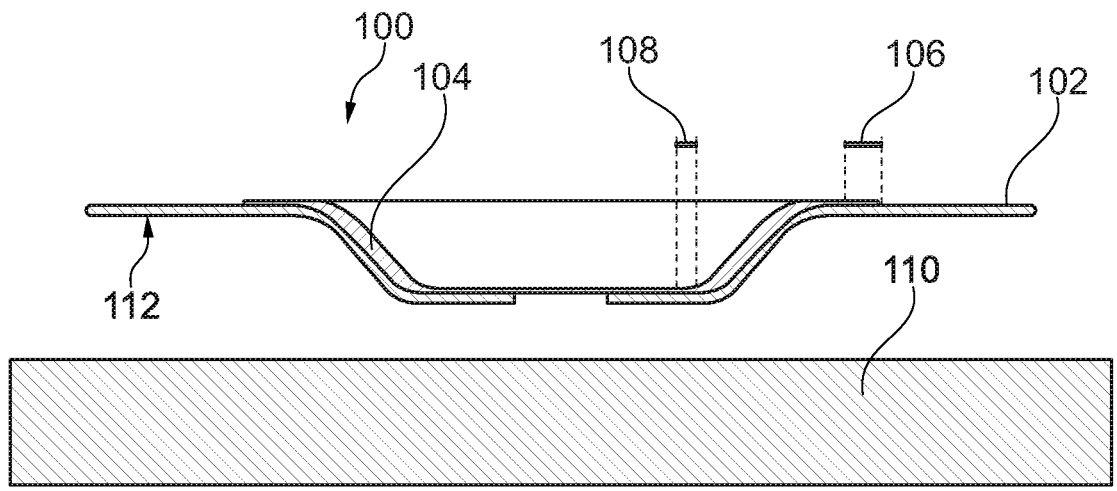

FIG. 1 discloses a cross-sectional view of a base plate 100 comprising an adhesive wafer 102 and a convex supporting device 104. The convex supporting device 104 is secured to the adhesive wafer 102 in a first attachment zone 108 and in a second attachment zone 106. In the figures, the convex supporting device 104 and the adhesive wafer 102 are not secured to each other in the area between the first attachment zone 108 and the second attachment zone 106. This may especially be seen in FIG. 3.

Figure 2:
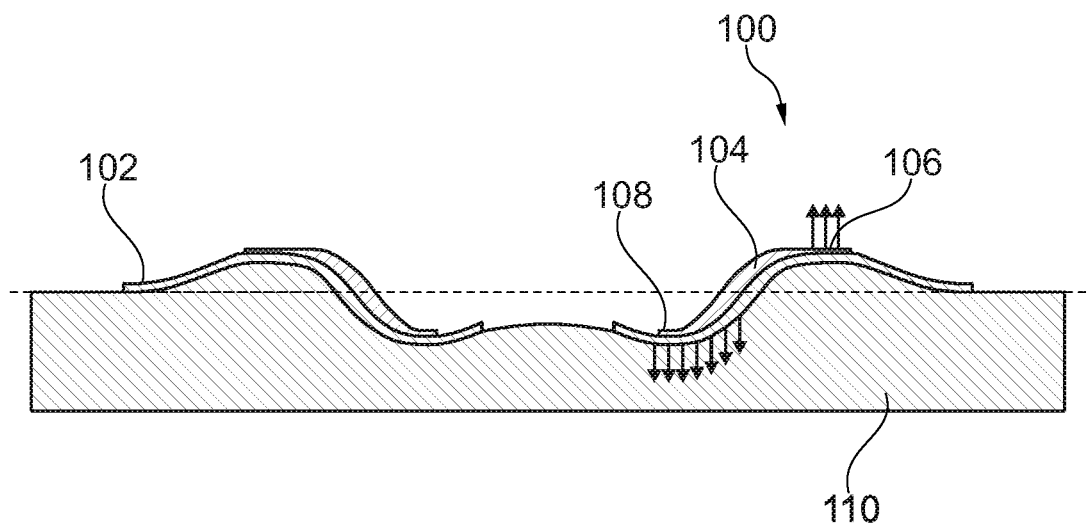
Figure 3:
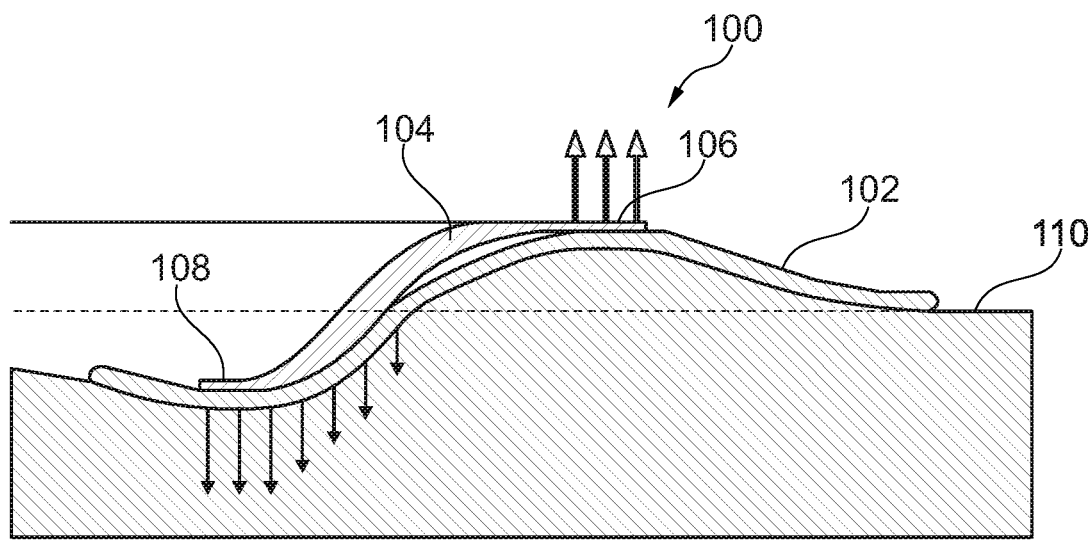

In FIGS. 2 and 3 the base plate 100 is secured to the skin 110 of a user by means of a skin friendly adhesive which is provided on a proximal side 112 of the adhesive wafer 102. Due to the convex shape of the convex supporting device 104, the base plate 100 is forced into contact with the skin 110 of the user substantially over its entire surface in cases where the stoma is provided in a concave cavity of the skin of the user.

Figure 4:
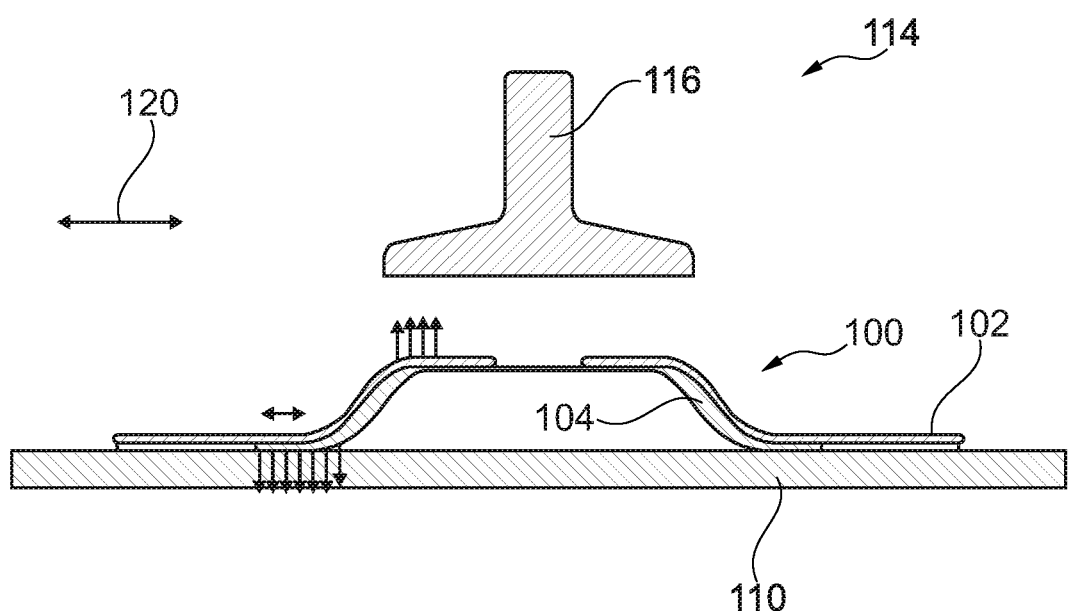

FIG. 4 discloses a testing device 114 for testing the axial compression resistance of the base plate 100. The testing device 114 comprises an upper axial testing part 116 and a lower axial testing part 118. During use, the base plate 100 is placed on the lower axial testing part 118 and the upper axial testing part 116 is moved towards the lower axial testing part 118 so as to incur a compression force on the base plate 100. In one embodiment, the base plate 100 is not retained in a transverse direction 120 during the test, whereby the compression force applied by the upper axial testing part 116 may cause a part of the base plate 100 to move in the transverse direction 120. In another embodiment, the base plate 100 is retained in the transverse direction 120, e.g. by adhering the base plate to the lower axial testing part 118 by means of the adhesive of the adhesive wafer 102.

During the test, the maximum or peak axial compression resistance is determined by determining the maximum reaction force the base plate 100 exerts on upper axial testing part 116 and/or the lower axial testing part 118 during testing.

Figure 5:
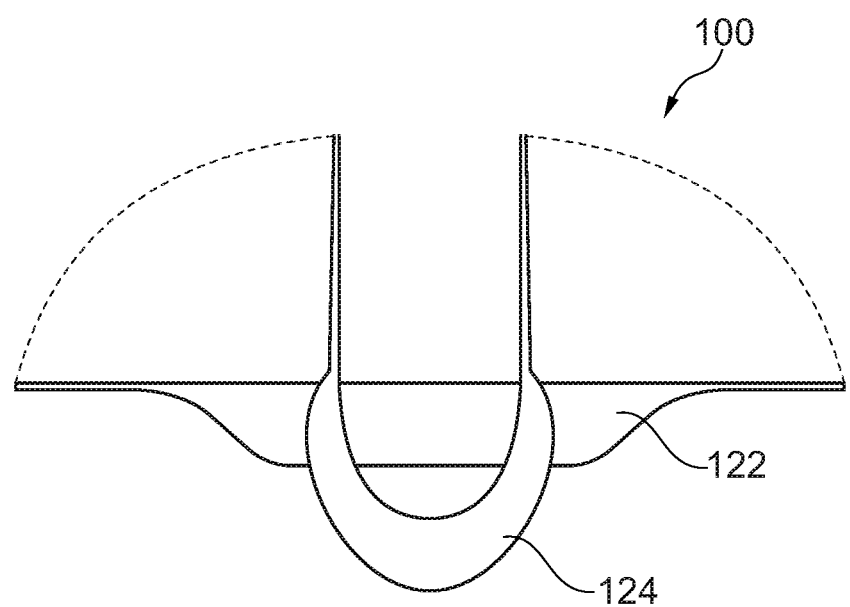
Figure 6:
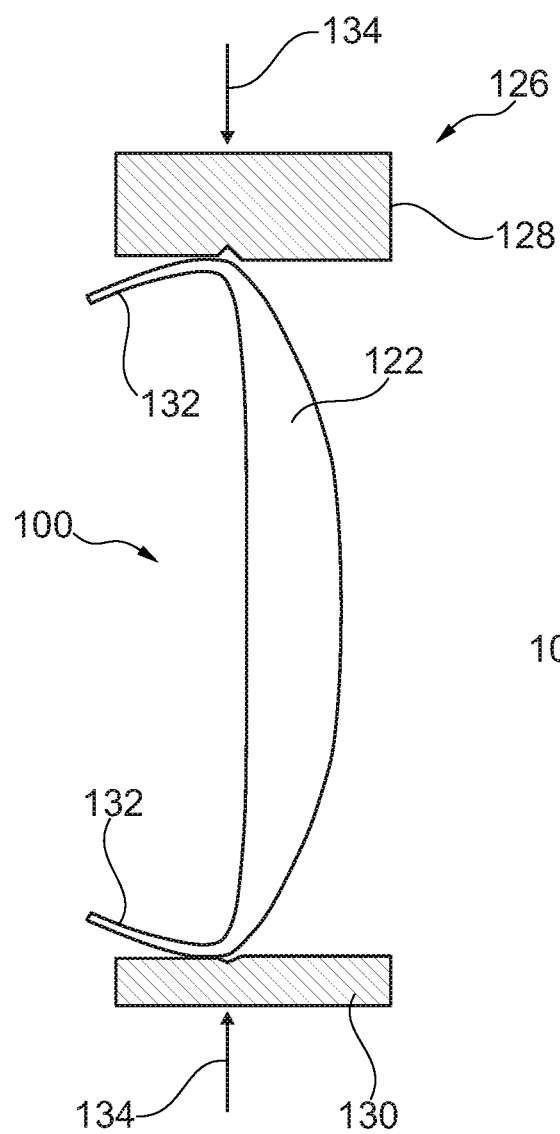
Figure 7:
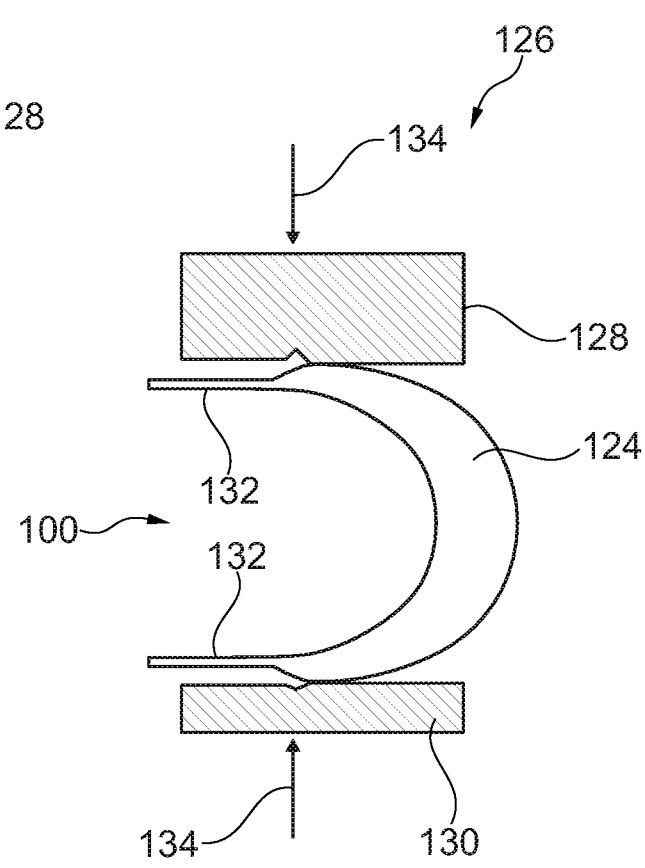

FIG. 5 discloses the base plate 100 in an unbent state 122 and in a bent state 124. The bending resistance may be determined by using the method described in relation to FIGS. 6 and 7.

Initially, a bending resistance testing device 126 is provided which comprises an upper bending testing part 128 and an lower bending testing part 130.

Next, the base plate 100 is provided and inserted into the bending resistance testing device 126. The base plate 100 is inserted into the bending resistance testing device 126 by folding a most radial part 132 of the base plate 100 such that the width of the base plate substantially corresponds to the width of the convex supporting device 104. The base plate 100 is inserted into the bending resistance testing device 126 such that it is retained between the upper bending testing part 128 and the lower bending testing part 130 without any further holding or securing means.

Subsequently, the upper bending testing part 128 and the lower bending testing part 130 are forced towards each other as is indicated by arrows 134. This causes the base plate 100 to be moved from the unbent state 122 which may be seen in FIG. 6, to the bent state 124 which may be seen in FIG. 7.

During the bending action, the reaction force exerted by the base plate on the upper bending testing part 128 and the lower bending testing part 130 is determined and the maximum value is determined. This value is used as a measure for the bending resistance. Alternatively, the force exerted on the upper bending testing part 128 and the lower bending testing part 130, once the two parts 128,130 have been moved a predetermined distance, may be used as a measure for the bending resistance.

Figure 8:
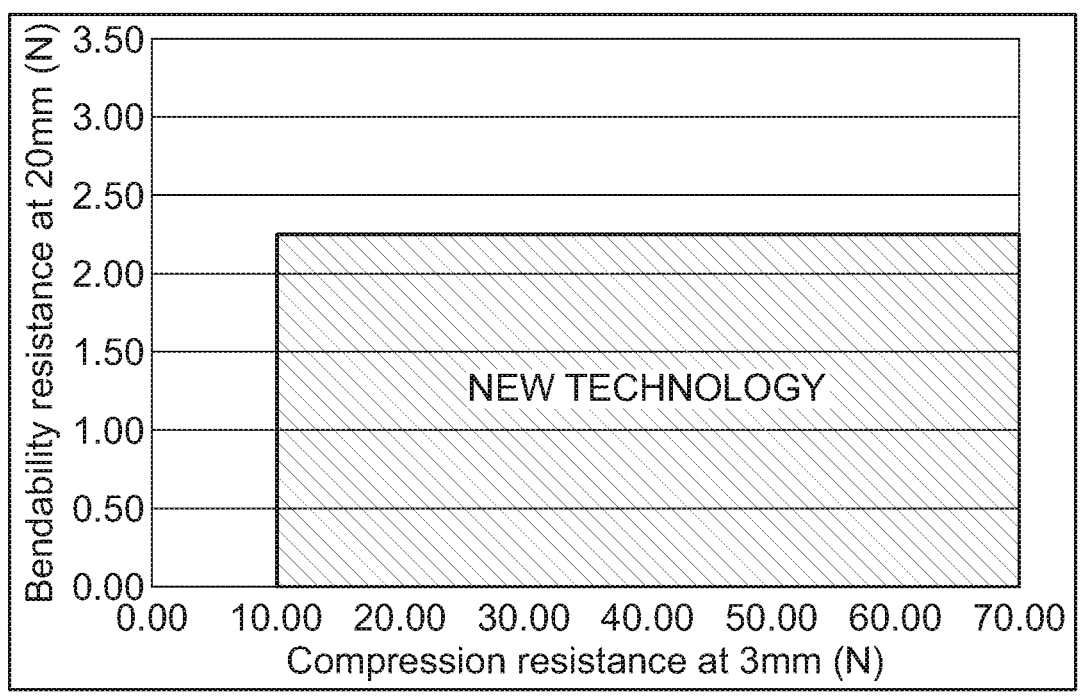

FIG. 8 basically schematically shows a relationship between the bendability resistance, shown in the vertical second (y)-axis, and the axial compression resistance, shown in the horizontal first (x)-axis scaled to illustrate the boundaries of the invention. In embodiments, any base plate according to the invention is located in the indicated "new technology" area.

EXAMPLES

In the following, a number of examples of convex supporting devices capable of achieving and controlling the axial compression resistance and/or bending resistance of the base plate of the invention are presented. The convex supporting device may also be referred to as a convex supporting element or a convex supporting member.

Example 1

Example 1 relates to a supporting device for stabilizing a skin area comprising a proximal annular element for placing around the skin area to be stabilized and a distal annular element axially offset from the proximal annular element, the proximal annular element and the distal annular element being interconnected by at least one resilient element.

The at least one resilient element allows for the annular elements to be axially displaced relative to each other, while still being biased towards a common neutral configuration. As understood in this example, the term resilient refers to a material or structure which is stretchable and compressible under application of a force, but which will return to its original shape when no force is applied.

This provides a device where a skin area may be stabilized and supported in order to, for example, provide rest or easy access, while still allowing the wearer to move around and perform everyday activities. Moreover, the flexibility of the supporting device reduces the risk of for example pressure wounds and generally increases the comfort for the wearer.

In the following, and in the application as a whole, it should be understood that the terms 'proximal' and 'distal' are used to describe relative orientation of objects and elements with reference to the surface of the skin. Thus, for example, the proximal annular element is closer to the skin than the distal annular element, and the proximal surface of the proximal annular element is the surface which faces the skin when the supporting device is worn, whereas the distal surface of the proximal annular element is the surface which faces away from the skin.

The at least one resilient element may be a spring element. This provides a simple way of providing flexibility and movement between the distal and proximal annular ring.

Alternatively or additionally, the at least one resilient element can be formed of a compressible material.

The supporting device can be applied to the distal side of the adhesive wafer, i.e. to the non-adhesive side.

The supporting device may have a convex shape thereby in itself forming a convex supporting device or it may be an integrated part of a convex device, e.g. a convex shell, in both instances forming a convex supporting device in a base plate of an ostomy appliance.

An embodiment of the example concerns a supporting device for stabilizing a skin area comprising a proximal annular element for placing around the skin area to be stabilized and a distal annular element axially offset from the proximal annular element, the proximal annular element and the distal annular element being interconnected by at least one resilient element.

Another embodiment of the example concerns a supporting device, wherein the at least one resilient element is a spring element.

Another embodiment of the example concerns a supporting device, wherein the at least one resilient element is formed of a compressible material.

Another embodiment of the example concerns a base plate for an ostomy appliance comprising an adhesive wafer for adhering to the skin surrounding a stoma and comprising a through-going hole in the adhesive wafer for receiving said stoma, wherein the base plate further comprises a supporting device of the example's other embodiments.

Another embodiment of the example concerns a base plate, wherein the supporting device is integrated in a convex shell.

Another embodiment of the example concerns a base plate, wherein the supporting device is at least partly embedded in the adhesive wafer.

Another embodiment of the example concerns a base plate, wherein the supporting device is applied to the distal side of the adhesive wafer.

Details of Example 1

Figure 9:
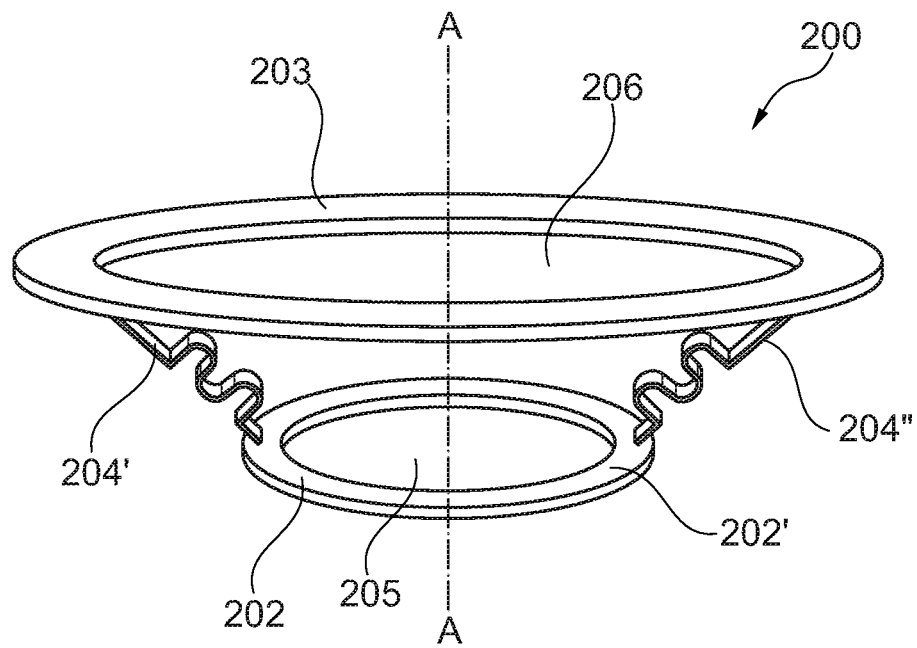
FIG. 9 shows, in perspective, a supporting device according to example 1.

A supporting device 200 for supporting a skin area is shown in FIG. 9. The supporting device has a proximal annular ring 202. The proximal annular ring 202 is connected to a distal annular ring 203 via spring element 204' and 204".

The proximal annular ring is formed as a circular ring and has a proximal through-going hole 205 which has a size suitable for enclosing a desired skin area, for example a stoma or a wound site.

The distal annular ring is also formed as a circular ring and has a distal through-going hole 206. The distal annular ring has a larger circumference than the proximal annular ring. This allows for easy access to the proximal through-going hole 205 through the distal through-going hole 206.

The proximal annular ring 202 and the distal annular ring 203 are displaced along the longitudinal axis A-A which extends through the centres of both the annular rings.

The proximal annular ring 202 and the distal annular ring 203 are connected via the spring elements 204' and 204". The spring elements extend from the proximal surface 203" of the distal annular ring and connects to the proximal annular ring 202 on its distal surface 202'.

The spring elements 204' and 204" are resilient in at least the longitudinal direction along the longitudinal axis A-A. Thus, the proximal annular ring 202 and the distal annular ring 203 may be pressed towards each other or pulled away from each other in an axial direction along the axis A-A. However, the spring elements force them back into alignment and position when no force is applied to the supporting device. Accordingly, when applied the supporting device will be biased to a neutral position wherein the annular rings are in desired position relative to each other.

Figure 10:
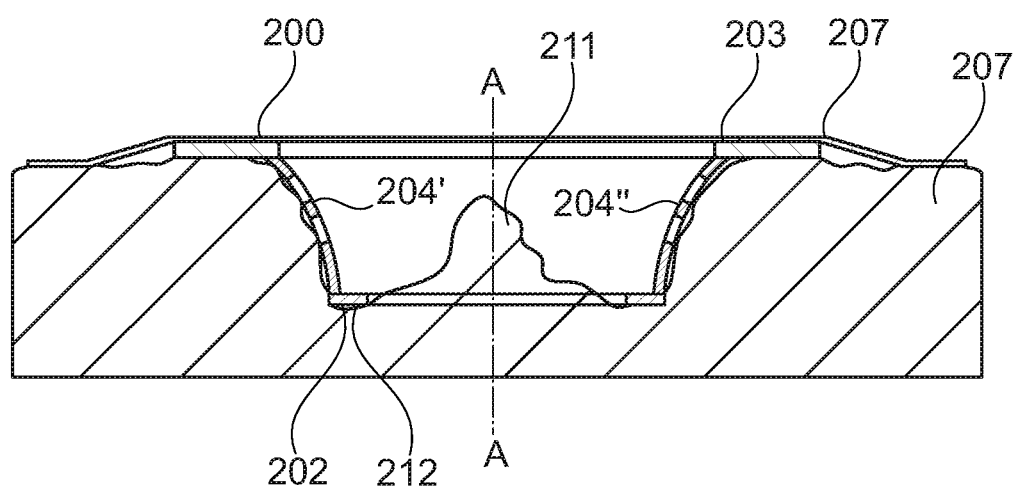
FIG. 10 shows, in section, the supporting device of FIG. 9 applied around a stoma.
Figure 11:
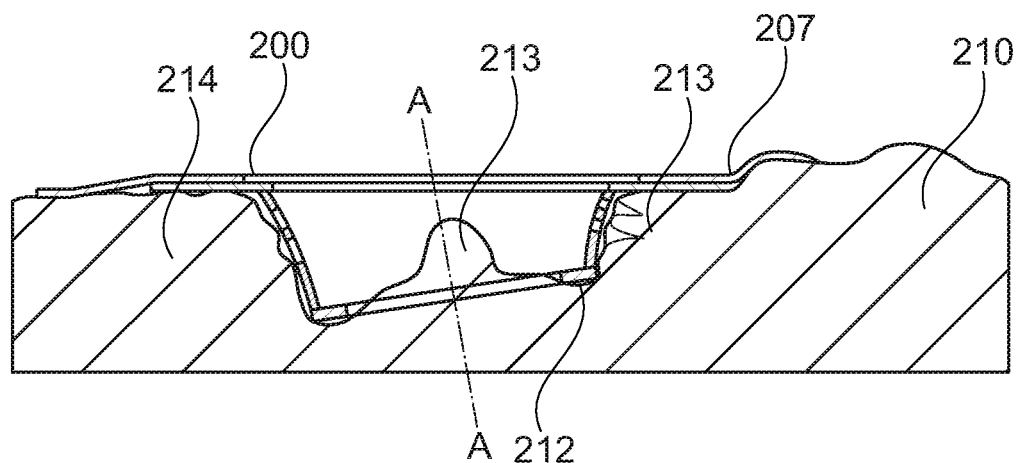
FIG. 11 shows the supporting device according to FIGS. 9 and 10 when the peristomal skin area around the stoma is moved.

FIGS. 10 and 11 illustrate, in section, the supporting device 200 attached to the skin 210 of a human being in order to support and stabilize the area around a stoma 211.

In FIGS. 10 and 11, the supporting device 200 is applied so that the proximal annular ring 202 presses against the peristomal skin area 212, i.e. the skin surrounding the stoma. The distal annular ring 203 is held against the skin 202 by an adhesive wafer 207. Alternatively or additionally, a belt (not shown) may be used in order to keep the supporting device pressed against the skin. By pressing the distal annular ring 203 against the skin, force is applied to the proximal annular ring 202 via the spring elements 204' and 204".

By dimensioning the spring elements 204' and 204", it is possible to obtain a necessary pressure on the peristomal skin area. Different pressure forces may be necessary in order to adapt the specific supporting device to a specific user. The specific user may need customized supporting devices in order to take into account the different conditions of the skin, such as the topography, for example scars and wounds. Thus, some users only require a low force, while others may require much higher pressure. A number of parameters may be altered in order to change the pressure force, for example the material of the spring elements can be changed or the thickness or other dimensions can be altered.

When the proximal annular ring 202 presses against the peristomal skin area, the pressure causes a slight lifting of the stoma, or put differently, the protuberance of the stoma in relation to the peristomal skin is increased. This facilitates access to the stoma and the skin within the proximal through-going hole when, for example, cleaning or inspecting the stoma as well as during the use. The increased protruding of the stoma ensures that stomal output coming out of the stomal opening is directed more securely to the inside of for example a collecting bag (not shown) which can be attached to the supporting device or to a base plate comprising the supporting device.

Moreover, this construction of the supporting device and application also keeps the stoma protected as the proximal annular ring provides increased stiffness thereby reducing the risk of strangulation or collapsing of the stoma or the immediate surrounding skin area. This kind of problem is often, but not exclusively, seen in relation to obese users where skin folds tend to close off the stoma or peristomal area. The stiffness of the proximal and distal annular rings may be modified in order to provide an appropriate balance between stiffness and flexibility in order to accommodate the needs of respective users. Consequently, the ability of the supporting device to resist bending and/or axial compression can be differentiated according to user needs.

This is, for example, an advantage when the users move around, thereby folding and stretching the skin as shown in FIG. 11, where the supporting device 200 is shown when the user for example bends. Such a bend creates a fold in one side 213 and a stretch in the other side 214. The spring elements 204' and 204" absorb both the flexing and the folding. The proximal annular ring prevents the skin fold in and over the stoma.

Figure 12:
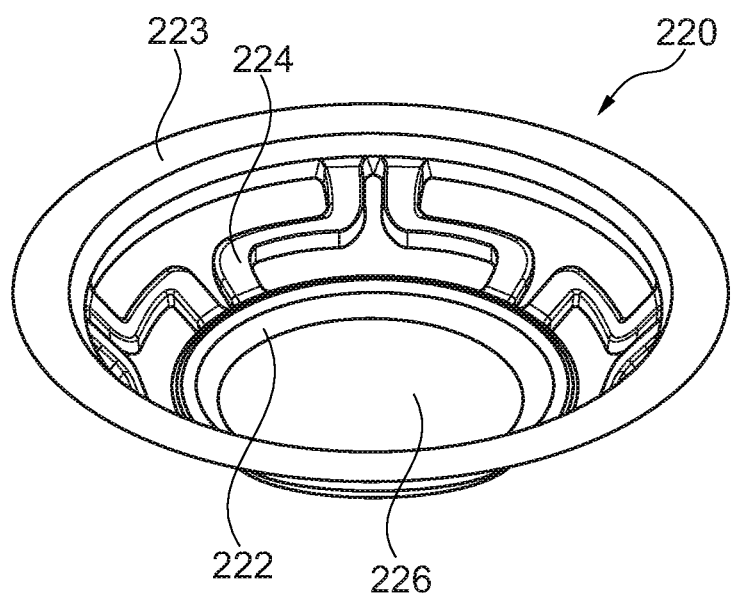
FIG. 12 shows, in perspective, a sub-example according to example 1.

An additional sub-example of a spring element based supporting device 220 is shown in FIG. 12. Similar to the example of FIGS. 9-11, the supporting device is formed of a proximal annular ring 222 and a distal annular ring 223. The proximal and distal annular rings are interconnected by eight spring members 224. This provides improved stability.

Figure 13:
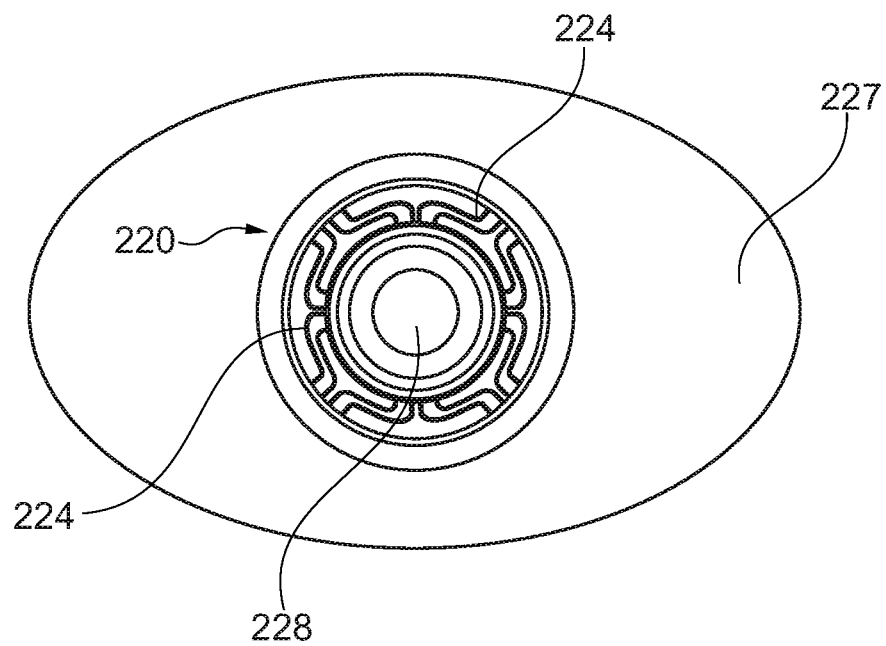
FIG. 13 shows a top view of the supporting device of FIG. 12 embedded in the adhesive of an adhesive wafer.
Figure 14:
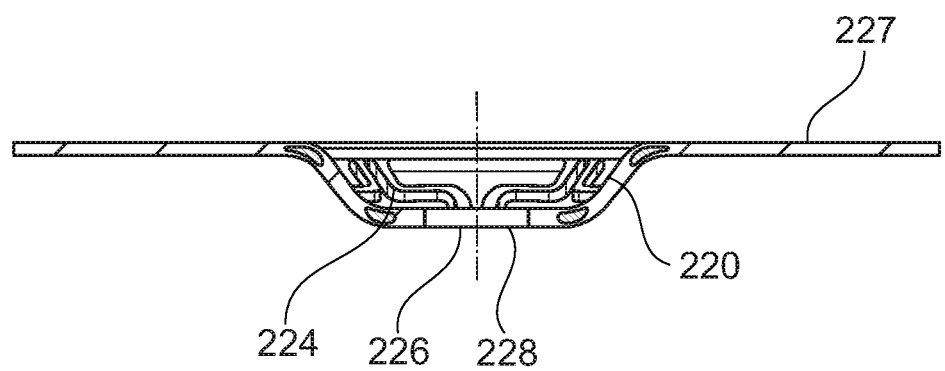
FIG. 14 shows a sectional view of the supporting device of FIG. 13.
Figure 15:
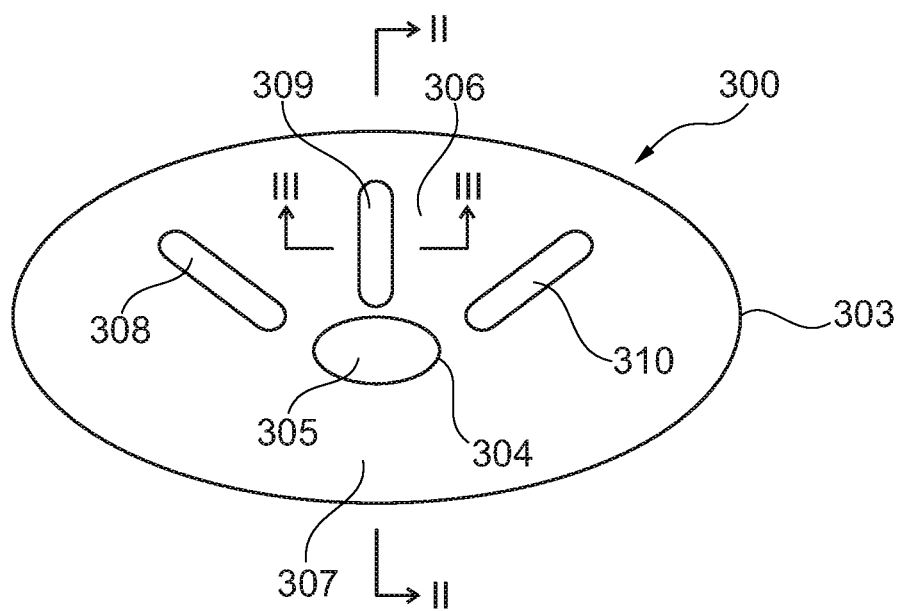
FIG. 15 shows a supporting member according to example 2.

FIGS. 13 and 14 show how the supporting device 220 of FIG. 12 may alternatively be embedded into the adhesive 225 of an adhesive wafer 227 or base plate of an ostomy appliance with their through-going holes 226 and 228 aligned.

Example 2

Example 2 relates to a supporting member connected to a base plate of an ostomy device. The supporting member comprises an annular ring defined by an outer edge and an inner edge defining a through-going hole having a central axis C-C, said ring comprising at least one stiffening element extending radially from the through-going hole towards the outer edge of the annular ring.

This provides stiffening of the base plate in selected areas, which is advantageous in order to prevent collapsing around the stoma when the wearer moves in specific positions where the risk of collapse is high. However, at the same time, flexibility and thereby high comfort may still be maintained.

The supporting member can advantageously be a convex shell wherein the outer edge and the inner edge are placed in separate planes offset in respect to each other along a central axis.

The stiffening element can be provided by forming the at least one stiffening element in the form of a groove formed in the annular ring. The groove can, for example, have a U-shape when seen in cross-section. The groove can be formed when the supporting member is formed, for example by injection moulding or it can be provided afterwards for example by pressure forming the grooves into the annular ring.

An inner circumference of the supporting member defined by its inner edge can be eccentrically arranged with respect to an outer circumference defined by its outer edge. This results in the distance between the outer and inner edge differing around the circumferential extent of the annular ring. This provides differentiated flexibility around the annular ring as larger areas, i.e. where the distance between the outer and inner edge is greater, will be stiffer and thus have a higher resistance against collapsing. Consequently, the ability of the supporting element to resist bending and/or axial compression can be differentiated according to user needs.

An embodiment of the example concerns a supporting member for use in a base plate of an ostomy device, the supporting member comprising an annular ring defined by an outer edge and an inner edge defining a through-going hole having a central axis C-C, said ring comprising at least one stiffening element extending radially from the through-going hole towards the outer edge of the annular ring.

Another embodiment of the example concerns a supporting member, wherein the supporting member is a convex shell in which the outer edge and the inner edge are placed in separate planes offset in respect to each other along the central axis C-C.

Another embodiment of the example concerns a supporting member, wherein the at least one stiffening element is in the form of a groove formed in the annular ring.

Another embodiment of the example concerns a supporting member, wherein the groove is U-shaped in cross-section.

Another embodiment of the example concerns a supporting member, wherein an inner circumference defined by the inner edge is eccentrically arranged with respect to an outer circumference defined by the outer edge.

Details of Example 2

FIGS. 15-18 show a supporting member 300 having the advantages as described herein.

The supporting member 300 is in the form of an annular ring which is defined by an outer edge 303 and an inner edge 304. The inner edge 304 also defines a through-going hole 305 through which a stoma can be received when the supporting member is incorporated into a base plate for use in an ostomy appliance.

The through-going hole defines an axis C-C, corresponding to the central axis of the inner edge. The inner edge 304 is eccentrically placed in respect to the outer edge 303, thereby dividing the supporting member 300 into two areas, i.e. a first area 306 where the radial distance from the inner edge to the outer edge is larger than in a second area 307.

Figure 17:
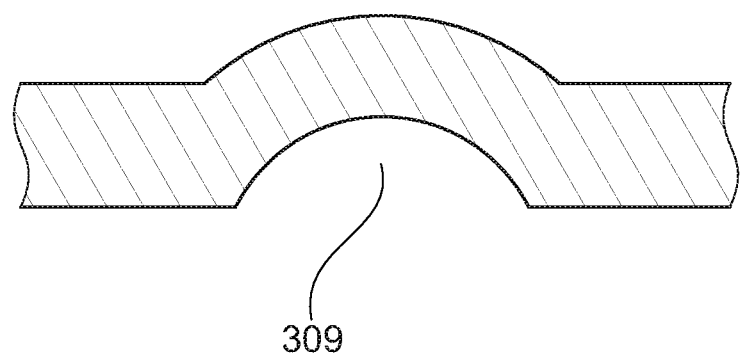
FIG. 17 shows the supporting member of example 2 in section along lines III-III in FIG. 15.

Three stiffening elements 308, 309, 310 extend radially from the inner edge 304 towards the outer edge 303 in the first area 306. The stiffening elements are formed as grooves in the supporting member 300 having a U-shape when seen in cross-section, as can be seen in FIG. 17. This increases the stiffness of the first area 306, thereby reducing the risk that the first area 306 of the supporting member 300 collapses onto a stoma protruding through the through-going hole 305.

Figure 18:
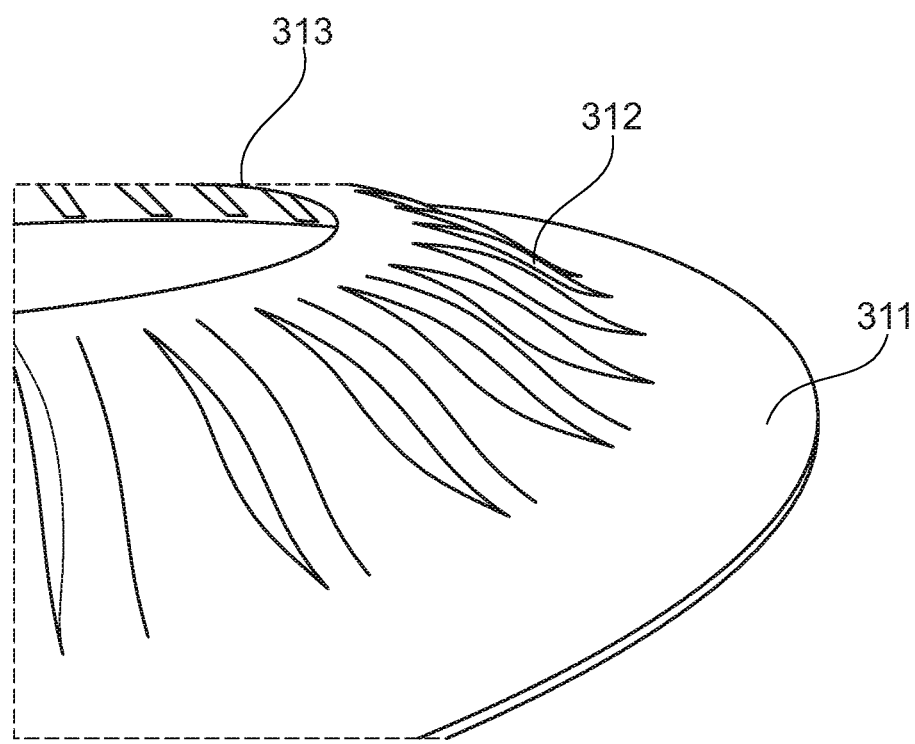
FIG. 18 is a perspective view of a detail of a supporting member.

The stiffening elements may also be solid so as not to form grooves as seen in the sub-example of FIG. 18. The stiffening elements 312 may project or extend axially from the proximal surface 311 of the convex supporting device, as is the case with the U-shaped groove of FIGS. 15-17, but instead of the U-shape they are completely solid thereby leaving no holes or irregularities in the distal surface 313 of the convex supporting device. The solid stiffening elements 312 may, however, still be relatively soft or resilient so that their contribution to the bending resistance of the convex supporting device in the horizontal bending direction is negligible.

The stiffening elements 312 may not only reduce the risk of the supporting element 300 collapsing onto a protruding stoma, they may also reduce the risk or effectively prevent that the pressure force from the peristomal skin causes the base plate with the convex supporting device to "turn inside-out" and/or consequently dislodge from the body. In the event that the ostomate subjects his/her body to a more extreme movement (such as reaching high or deep down, or during physical exercise), the pressure force from the peristomal skin area on the base plate may momentarily rise to a higher level than in the normal wear situation and may consequently push the base plate away from the body in the peristomal area. As the base plate is adhered to the body over a larger area than what corresponds to the peristomal skin area, the result may be that the base plate with the convex supporting device flips or "turns inside-out" in the peristomal area, but remains attached at the edge. This is of course not desirable as it would almost certainly lead to leakage and a need to change the product. To avoid this situation, the described solid stiffening elements 312 may be comprised in the convex supporting device.

Figure 16:
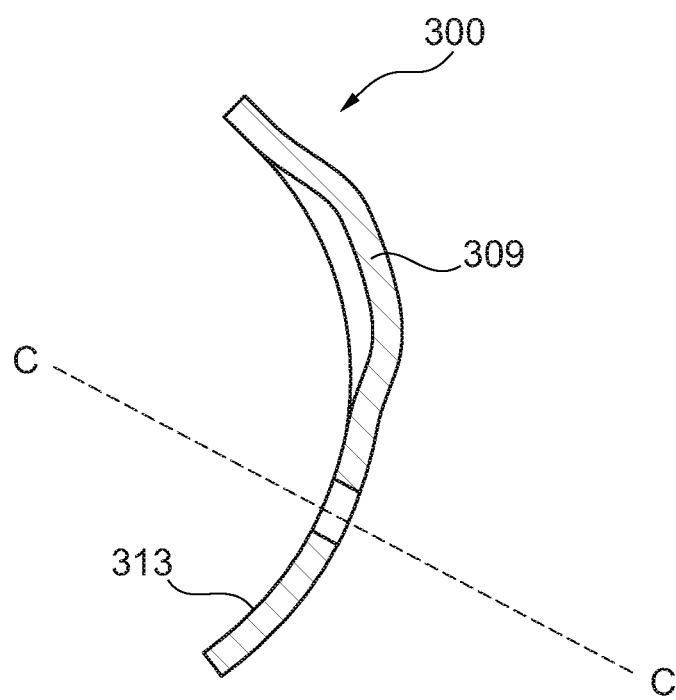
FIG. 16 shows the supporting member of example 2 in section along lines II-II in FIG. 15.

In order to accommodate sunken or retracted stomas, the supporting member has a convex shape, which can be seen in FIG. 16. Basically, when referring to a convex shape or element in respect of ostomy devices reference is often made to an insert or an element where the two outer edges, e.g. the outer edge 303 and inner edge 304 of example 2, are displaced axially along the centre axis C-C, which also corresponds to the axis along which the stoma extends longitudinally when the ostomy appliance is worn.

Example 3

Example 3 relates to a base plate for an ostomy appliance comprising an adhesive wafer for adhering to the skin surrounding a stoma, the base plate comprising a supporting element attached to the distal side of the adhesive wafer, the supporting element comprising a proximal annular element for placing around the stoma and at least two supporting arms extending radially from the outer edge of the proximal annular element and extending axially from the proximal annular element in the distal direction.

This provides a base plate which provides support around the stoma and support in a relevant, desired skin area to provide increased comfort and security.

Thus, in a specific version of example 3, two supporting arms extend diametrically opposite from the proximal annular element. This allows for a wearer to bend around the supporting arms without experiencing discomfort, while at the same time it decreases the risk of the base plate unintentionally folding in other directions. By the diametrically opposite extension of the supporting arms is to be understood that each of the arms extend radially away from the proximal annular element to which they connect.

An embodiment of the example concerns a base plate for an ostomy appliance comprising an adhesive wafer for adhering to the skin surrounding a stoma, the base plate comprising a supporting element attached to the distal side of the adhesive wafer, the supporting element comprising a proximal annular element for placing around the stoma and at least two supporting arms extending radially from the outer edge of the proximal annular element and extending axially from the proximal annular element in the distal direction.

Another embodiment of the example concerns a base plate comprising two supporting arms extending diametrically opposite from the proximal annular element.

Details of Example 3

Figure 19:
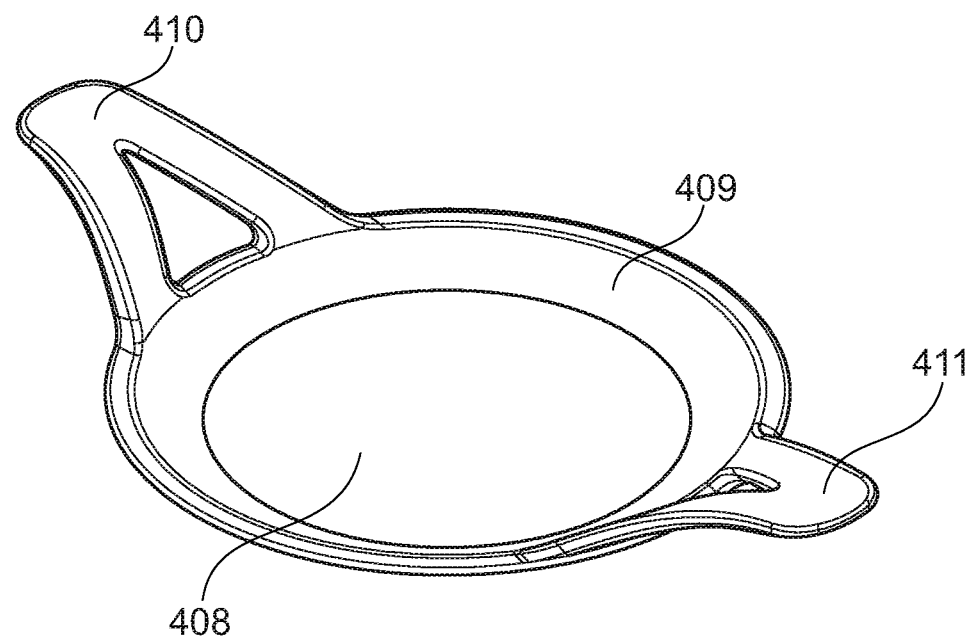
FIG. 19 shows a supporting element of example 3.
Figure 20:
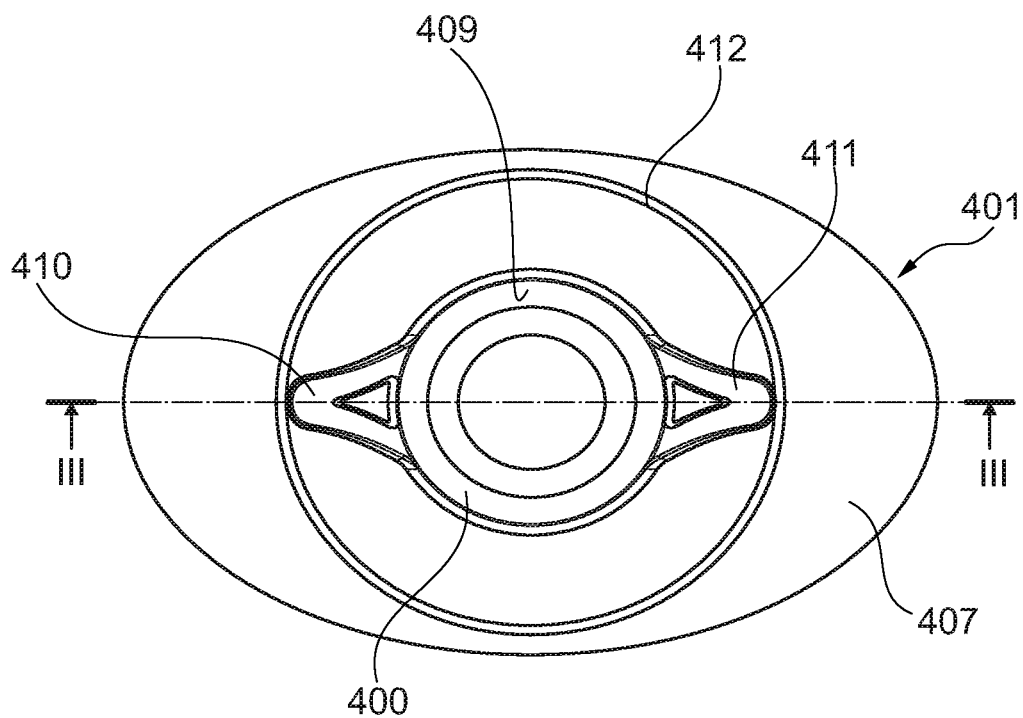
FIG. 20 shows a base plate having the supporting element of FIG. 19.
Figure 21:
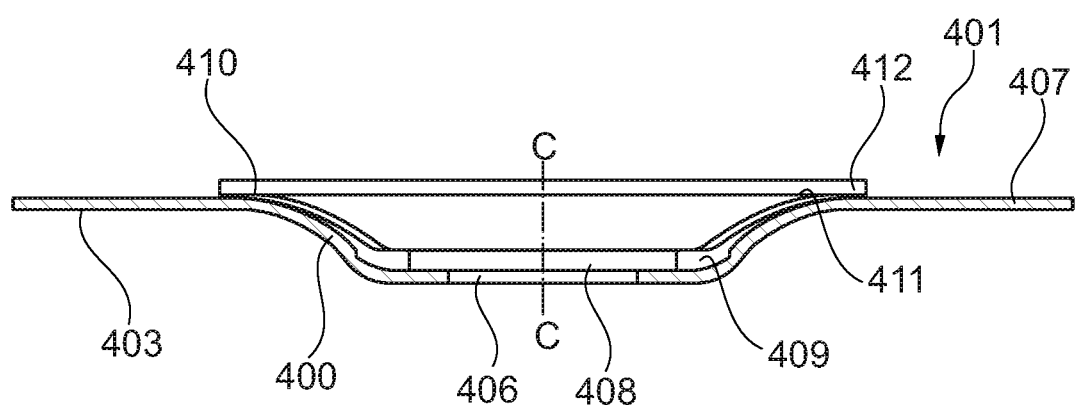
FIG. 21 shows the base plate with the supporting element of FIG. 19 in section along line III-III in FIG. 20.

FIG. 19 shows a supporting element 400, and FIGS. 20 and 21 show a base plate 401 formed of an adhesive wafer 407 and the supporting element 400. The adhesive wafer 407 has an adhesive 402 disposed on a backing layer 403 so that the adhesive wafer has an adhesive proximal surface and a non-adhesive distal surface.

The supporting element is attached to the non-adhesive distal surface by e.g. gluing or welding. The adhesive wafer 407 is formed with a first through-going hole 406 and the supporting element has a second through-going hole 408. The adhesive wafer and the supporting element are aligned so that the first and second through-going holes are coaxially aligned along a central axis C-C. This allows for a stoma to be received by the base plate 401.

The supporting element is formed by an inner annular ring 409, which provides support and stability to the skin area encircled by the ring which corresponds to the second through-going hole 408.

Two arms 410, 411 extend on opposite sides of the inner annular ring 409. The arms allow for flexibility when the base plate is folded or bent around the respective arms but have or incur a higher stiffness or rigidity if the base plate is folded or bent transversely to the extent of the respective arms.

In order to provide additional support, the arms also extend in an axial direction, i.e. along or parallel to the central axis C-C defined by the two through-going holes 406, 408. This provides arms that slant in an axial direction and thereby provides axial stability to the base plate.

In order to attach a collecting bag to the base plate in the event of a 2-piece product, a coupling ring 412 is shown attached to the distal side of the adhesive wafer.

It should be understood that the arms can have numerous shapes and configurations. For example, in one embodiment, the two or more supporting arms are provided in a bifurcated configuration extending from the proximal annular element. This allows for an even further differentiated effect of the supporting element, while still providing increased comfort and security in a desired, relevant skin area. Consequently, the ability of the supporting element to resist bending and/or axial compression can be differentiated according to user needs.

Example 4

Example 4 relates to a convex shell for use in a base plate of an ostomy appliance, the convex shell comprising an annular ring defined by an outer edge and an inner edge defining a through-going hole, said annular ring comprising a first and second half defined by a folding axis A-A, which is perpendicular to the centre axis C-C of the through-going hole, wherein the convex shell comprises first folding restriction means for altering the flexibility of the convex shell when the first half is folded toward the second half around the folding axis A-A.

Having a flexibility that can change depending on the folding angle, it is possible to provide an ostomy device which is soft and comfortable when regular movement of the body occurs, but where it is possible to prevent that the skin area around the stoma collapses in outer, or extreme, movement positions.

Thus, for example, the first folding restriction means provides a first flexibility when the angle between the first and second half is between 180 and 90 degrees and a second flexibility when the angle between the first and second half is between 90 and 20 degrees, wherein the first flexibility is lower than the second flexibility.

In this context, the phrase "lower" in regard to flexibility should be understood such that the resulting reactive force of the convex shell when the folding angle between the first and second half is between 180 and 90 degrees is less than the resulting reactive force of the convex shell when the folding angle between the first and second half is between 90 and 20 degrees.

Accordingly, as long as the movement of the body folds the ostomy device in the range of the first folding angle then the ostomy device will be comfortable to wear and follow the movement of the body. However, if movement results in the ostomy device being folded in the range of the second folding angle, the ostomy device will provide a reinforced stiffness to the area around the stoma providing stability to the peristomal area.

More specifically, the first folding restriction means may be in the form of at least one groove extending along the first axis, said groove having two opposite contact surfaces which are able to abut each other when the convex shell is folded, or bent, to a predetermined degree around the first axis.

This provides a high flexibility as long as the two opposite contact surfaces are not abutting each other. However, if a fold, or bending movement of the user, causes the two contact surfaces to abut, the force required to further fold, or bend, the convex shell increases considerably providing a high stiffness and support around the stoma.

The first folding restriction means on the convex shell may be placed on either side of the annular ring, i.e. both on the side facing the ostomist when the product is in use and/or on the side facing away from the ostomist.

In embodiments wherein the first folding restriction means is/are placed on the side facing the user, there may be provided a distance between the convex shell and the base plate of the ostomy appliance in the area between the inner and the outer edge of the annular ring, thus creating a volume between the two parts when the annular ring is attached to the base plate of the ostomy appliance at said edges. Furthermore, or alternatively, there may be extra adhesive material in the base plate over at least some of the base plate area situated between the inner and outer edge of the annular ring.

These features ensure that the flexibility of the base plate is maintained because the adhesive material of the base plate can deform, e.g. stretch and/or follow the body movements of the user independently of the characteristics of the convex shell in that area.

An embodiment of the example concerns a convex shell for use in a base plate of an ostomy appliance, the convex shell comprising an annular ring defined by an outer edge and an inner edge defining a through-going hole, said annular ring comprising a first and second half defined by a folding axis A-A, which is perpendicular to the centre axis C-C of the through-going hole, wherein the convex shell comprises first folding restriction means for altering the flexibility of the convex shell when the first half is folded toward the second half around the folding axis A-A.

Another embodiment of the example concerns a convex shell, wherein the first folding restriction means provides a first flexibility when the angle between the first and second half is between 180 and 90 degrees and a second flexibility when the angle between the first and second half is between 90 and 20 degrees, and wherein the first flexibility is lower than the second flexibility.

Another embodiment of the example concerns a convex shell, wherein the first folding restriction means is in the form of at least one groove extending along the first axis, said groove having two opposite contact surfaces which are able to abut each other when the convex shell is folded to a predetermined degree around the first axis.

Details of Example 4

Figure 22:
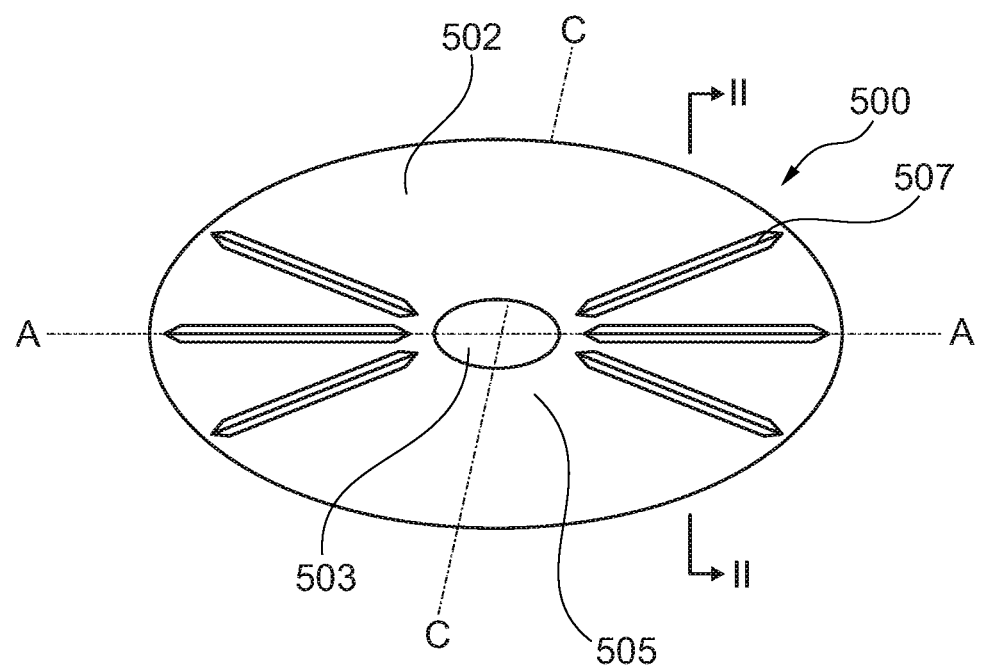
FIG. 22 shows a convex shell having folding restriction means according to example 4.
Figure 23:
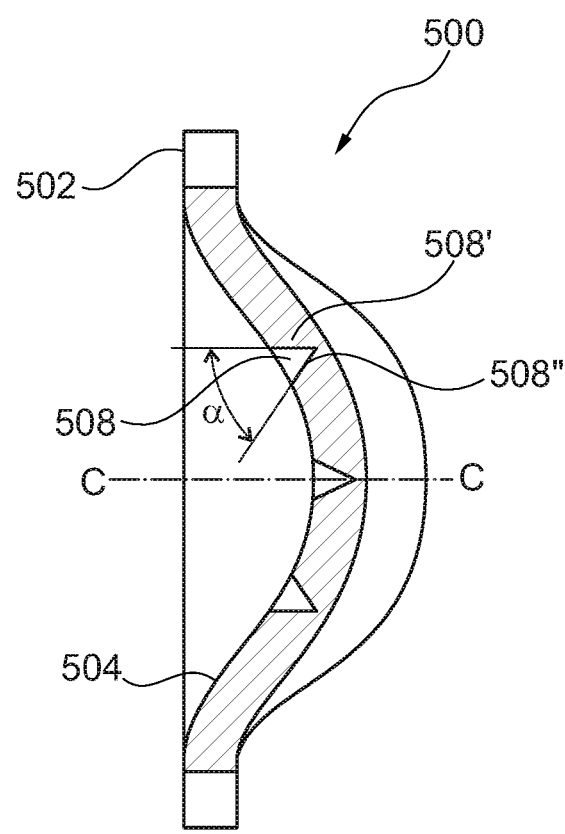
FIG. 23 shows the convex shell of FIG. 22 in section along line II-II in FIG. 22.

A convex shell 500 for use in a base plate (not shown) for attaching an ostomy collecting pouch to a user's body is shown in FIGS. 22 and 23.

The convex shell 500 comprises an outer planar surface 502 extending in a first plane perpendicular to the centre axis C-C of a through-going hole 503 formed in the convex shell 500 for receiving the stoma, the outer planar surface 502 extending radially inwards from the outer edge and transitioning into an intermediate slanting surface 504. The intermediate slanting surface 504 extends radially inwards from the outer planar surface 502 towards an inner planar surface 505. The inner planar surface 505 extends in a second plane perpendicular to the centre axis C-C of the through-going hole 503 and extends radially from the intermediate slanting surface 504 towards an inner edge 506 of the convex shell 500 which defines the through-going hole 503.

Six folding restriction means 507 are formed as respective grooves 508 extending transversely across the convex shell 500 from the inner planar surface 505 to the outer planar surface 502. Each groove has a first and a second groove wall 508', 508" defining a folding angle α.

When the convex shell 500 is folded, or bent, around the folding axis A-A, which is perpendicular to the centre axis C-C, e.g. when a user bends, the two halves of the convex shell defined by the folding axis A-A will fold towards each other. At the same time, the groove walls 508' and 508" will also fold towards each other. This results in the folding angle α becoming smaller. At one point, if folded, or bent, to a certain extent, the groove walls 508' and 508" will contact each other when the folding angle reaches zero. At this point, the force required to fold or bend the convex shell 500 will increase considerably as the force needed to fold the convex shell also has to compress the material of the convex shell in order to fold it further.

Understanding that the material of the convex shell 500 affects the folding considerably when the two groove surfaces 508', 508" come into contact enables the skilled person to modify the flexibility or bending resistance of the convex shell in order to suit specific needs by using different materials having different compressible characteristics.

Should it be desirable to change the flexibility in further intervals the six grooves in the convex shell can be formed so that the respective groove walls have different angles between them. Thus, when grooves having one angle abut, the stiffness is increased slightly, and when grooves having a larger initial angle abut, the stiffness will increase even further.

Figure 24:
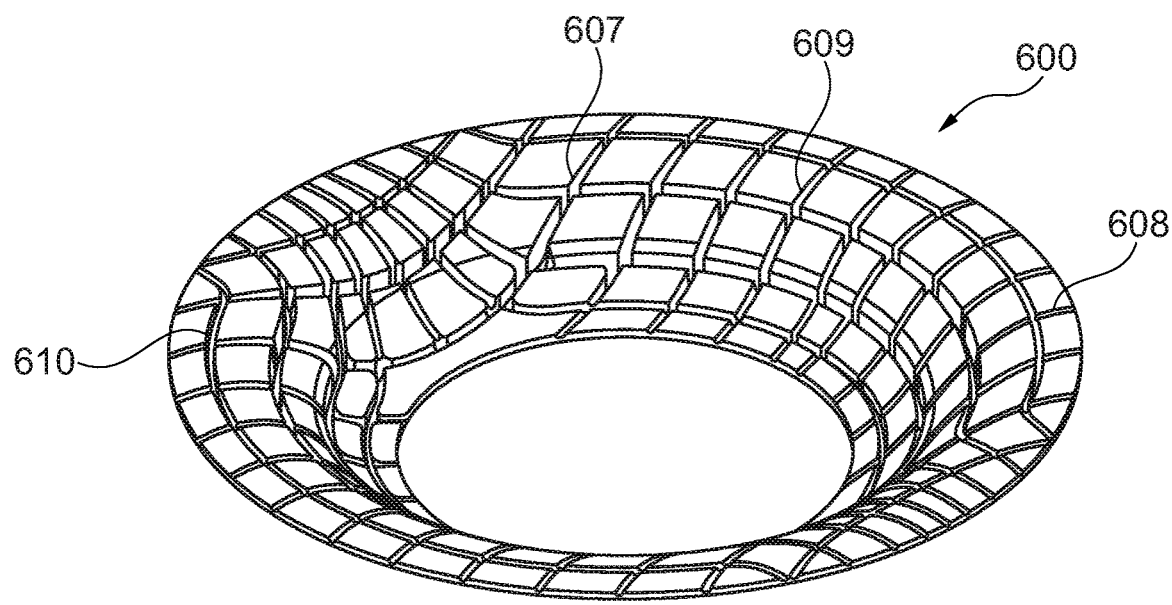
FIG. 24 shows another version of a convex shell as described in example 4.

A convex shell 600 having numerous restriction means 607 is shown in FIG. 24. The restriction means are in the form of grooves 608, where a number of first grooves 609 extend in one direction across the convex shell and a number of second grooves 610 extend in another direction transverse to the direction of the first grooves.

Example 5

Example 5 relates to a convex shell for use in a base plate of an ostomy appliance, the convex shell comprising an annular ring defined by an outer edge and an inner edge defining a through-going hole, said ring further comprising at least four transition sections extending transversely across the annular ring, dividing the annular ring into at least a first, second, third and fourth segment.

From the term it should be understood that a 'transition section' is a section wherein the characteristics between two neighbouring segments of the convex shell changes.

By changing the characteristics of the convex shell in such sections, it is possible to control the bending of the shell and, as will be described herein, it will be possible to keep the area around the stoma more stable and resistant towards collapsing, while providing improved flexibility in the peristomal area for better comfort.

The transition sections can be provided as grooves.

The first, second, third and fourth segments can be arranged symmetrically. This can for example be done by arranging the first and third segments opposite each other, and the second and fourth segments opposite each other.

The first and third segments may have a higher thickness than the second and fourth segments. This is an additional and/or alternative way to control the bending. This results in that the convex shell will tend to bend in the transition sections where the thickness changes.

Alternatively, the first and third segments may be formed by a different material than the second and fourth segments, which is another way to control the bending.

Alternatively or additionally, the second and fourth segments may have a higher flexibility than the first and third segments.

Details of Example 5

Figure 25:
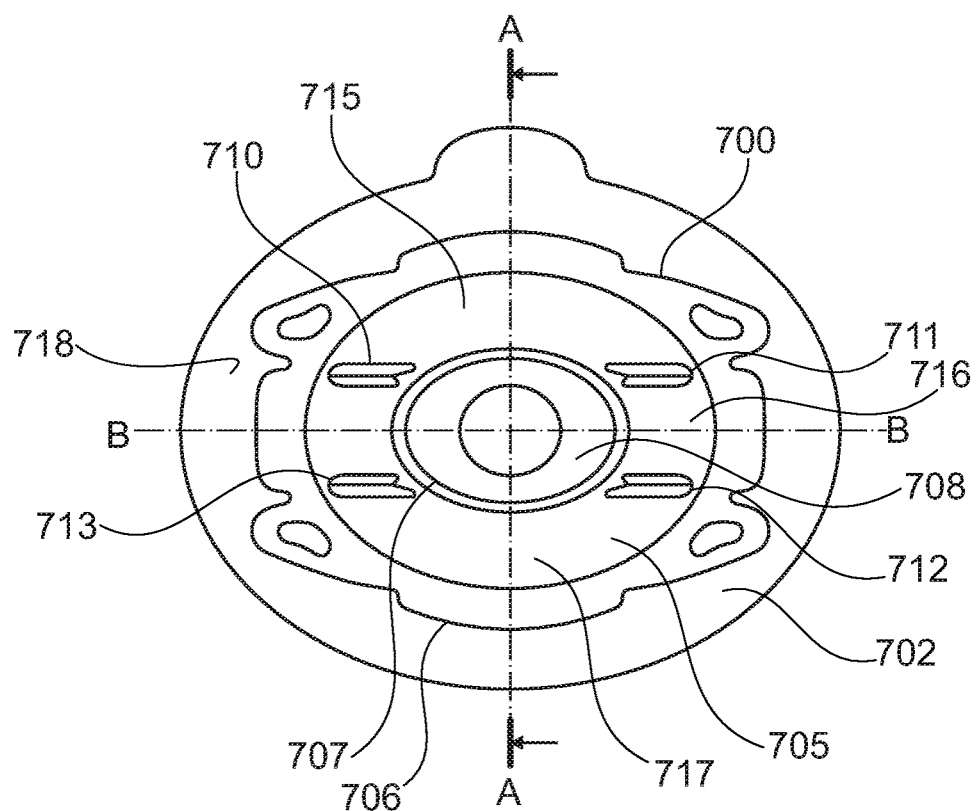
FIG. 25 shows a convex shell according to example 5.

The convex shell 700 of FIG. 25 comprises an annular ring 705 defined by an outer edge 706 and an inner edge 707. The inner edge 707 defines a through-going hole 708 which has an axis C-C. Furthermore, when considering the convex shell along the axis C-C of the through-going hole 708, the convex shell is symmetrical around axes A-A and B-B, which are perpendicular to each other.

In use, the convex shell will preferably be applied on a user so the axis A-A will be mainly vertical and the axis B-B will be mainly horizontal when a user is standing. Or, in other words, the convex shell will be applied so that the natural movements of the user will cause the convex shell, and thereby the convex skin plate, to bend around the axis B-B.

Four transition sections, formed as first, second, third and fourth grooves 710,711,712,713 extend transversely across the annular ring. The grooves divide the annular ring into at least a first segment 715 defined by the first and second grooves; a second segment 716 defined by the second and third grooves; a third segment 717 defined by the third and fourth grooves; and a fourth segment 718 defined by the fourth and first grooves.

A hole 720 is provided in the backing layer 702 and adhesive 703 which is coaxially aligned with the through-going hole 708 of the convex shell.

Figure 26:
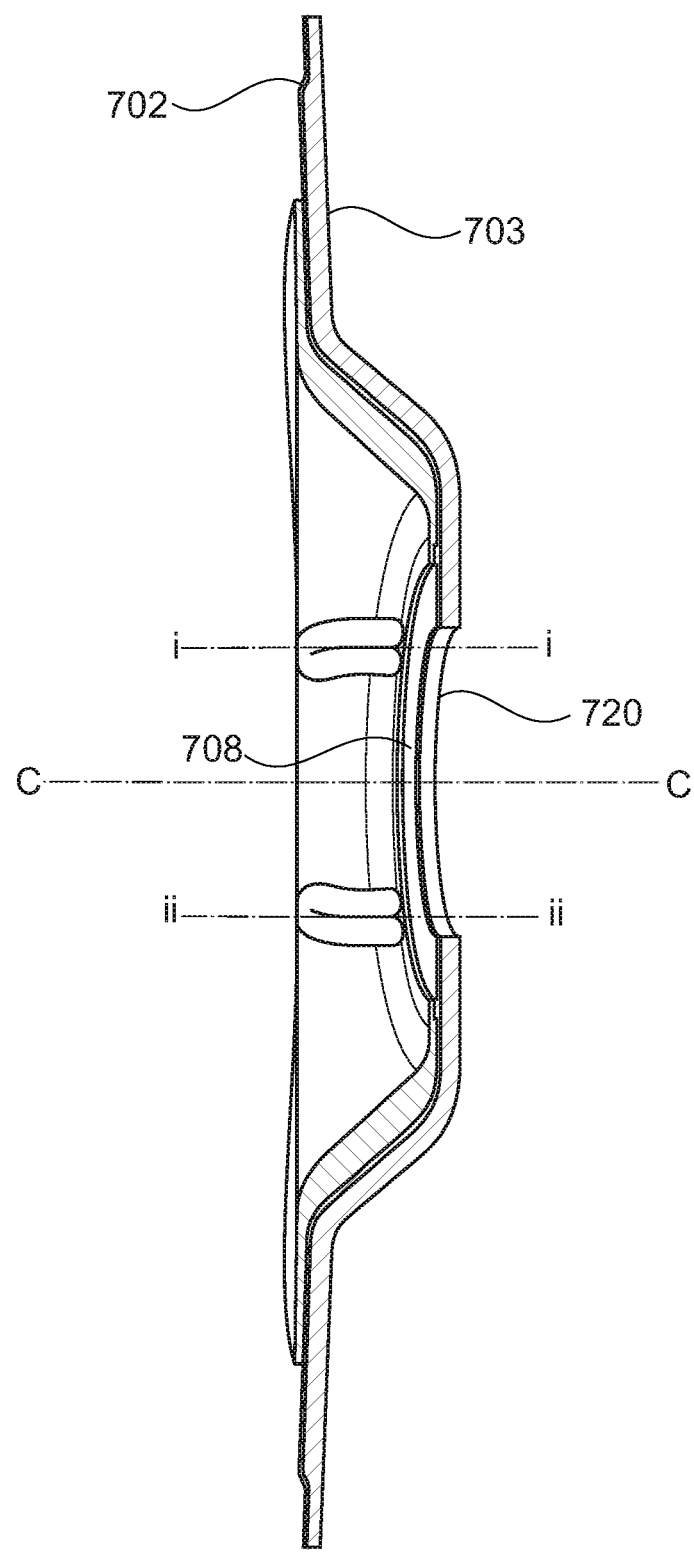
FIG. 26 shows a sectional view of the convex shell of FIG. 25 along line A-A of FIG. 25.

As can be seen in FIG. 26, the first groove 710 extends along an axis i-i and the fourth groove 713 extends along an axis ii-ii. In a similar way, although not shown, the second groove 711 extends along the axis i-i, and the third groove 712 extends along the axis ii-ii.

It is to be understood that the features and principles of the presented examples of the application can be applied individually or in any suitable combination to make a convex supporting device for the base plate according to the invention.

Example 6

Experimental Part

A number of bendability, or folding, resistance and axial compression resistance tests according to the described test methods were carried out on a number of products presently commercially available on the market and on the applicant's products according to the invention. The products and the test results are presented and compared in the following. The bendability and compression tests were carried out on a texture analyser TA.XT Plus, serial number 10663 from Texture Technologies using 1, 5 and 30 kg load cells in an air-conditioned laboratory at a constant temperature of 23 degrees Celsius and at constant 50% RH.

Products Tested:

B.Braun Softima 1-piece ileostomy Roll-Up w/convex appliance, pre-cut hole Ø30 mm Coloplast SenSura Convex Light appliance, pre-cut hole Ø15 mm-Ø33 mm(max)

Convatec Esteem 1-piece ileostomy Invisiclose w/convex appl., pre-cut hole Ø32 mm Dansac Nova 1, 1-piece closed colostomy appliance w/convex, pre-cut hole Ø28 mm Hollister Moderma Flex 1-piece urostomy appliance w/convex, pre-cut hole Ø15 mm Salts Confidence 1-piece colostomy appliance w/convex, pre-cut hole Ø28 mm Welland Flair 1-piece colostomy appliance w/convex, pre-cut hole Ø29 mm Prototype products with convex supporting device A, B, C, D, E and F.

The material for the convex supporting device of the prototype products is preferably primarily a polyethylene-based material, such as, but not limited to, Engage 8401® or Engage 8402® which are both polyolefin elastomers in the form of ethylene-octene copolymer from Dow Chemical or Flexirene®, a linear low density polyethylene (LLDPE) from Polimeri Europa. To further control characteristics, e.g. resiliency of the convex supporting device, additional materials such as, but not limited to, EVA copolymers e.g. Escorene® grades from ExxonMobil Chemical may be added.

The convex supporting device is produced by a classic plastic injection moulding process. Polymer material is fed into a heated barrel, mixed, and forced into a mould cavity where it cools and hardens to the configuration of the cavity. The backing layer, adhesive and release liner is further shaped to a convex shape to match the convex supporting device. The convex supporting device is placed on the backing layer and heat welded thereto at the outer and inner perimeter of the shell (corresponding to first and second attachment zones). During the heat welding process the convex supporting device and the backing layer are merged together as a result of pressure, heat and time.

Prototypes A and C are a base plate comprising a convex supporting device based on the principles of example 5 having an axial distance between the inner and outer edges of the annular ring measured along the central axis C-C of 7 mm.

Prototypes B and D are a base plate comprising a convex supporting device based on the principles of example 4 having an axial distance between the inner and outer planar surfaces of the convex shell measured along the central axis C-C of 9 mm.

Prototypes E and F are a base plate comprising a convex supporting device based on the principles of examples 4 and 5 in combination, the transition sections of example 5 being provided on the distal side of the convex supporting element and the folding restriction means of example 4 being provided on the proximal side of the convex supporting device. The axial distance between inner and outer edges of the annular ring of the convex shell measured along the central axis C-C is 9 mm.

The tests were carried out on two test specimens of each type of the products A, B, C and D and on one test specimen of types E and F (see additional comment in table 1 regarding Hollister Moderna Flex). The tested specimens did not include a release liner on the adhesive surface of the base plates. A very thin sheet of paper towel was applied to the adhesive surface in order to avoid unintentional adherence. The contribution to the bending and axial compression resistances, respectively, from this very thin and flexible component, are disregarded. Tables 1 and 2 show results of the axial compression test and the bendability test, respectively.

TABLE 2

| Test Specimen Product | Load [N] at 20 mm bending | Average bending load [N] | Standard deviation | Standard deviation [%] |
|---|---|---|---|---|
| B. Braun Softima Specimen 1 | 8.40 | 7.94 | 0.455 | 6 |
| B. Braun Softima Specimen 2 | 7.50 | | | |
| Coloplast SenSura Convex Light Specimen 1 | 9.20 | 8.20 | 1.008 | 12 |
| Coloplast SenSura Convex Light Specimen 2 | 7.19 | | | |
| Convatec Esteem Specimen 1 | 15.09 | 15.55 | 0.462 | 3 |
| Convatec Esteem Specimen 2 | 16.01 | | | |
| Dansac Nova Specimen 1 | 16.31 | 16.22 | 0.093 | 1 |
| Dansac Nova Specimen 2 | 16.13 | | | |
| Hollister Moderma Flex Specimen 1 | 18.56 | 19.14 | 0.577 | 3 |
| Hollister Moderma Flex Specimen 2 | 19.72 | | | |
| Salts Confidence Specimen 1 | 4.78 | 4.80 | 0.027 | 1 |
| Salts Confidence Specimen 2 | 4.83 | | | |
| Welland Flair Specimen 1 | 2.27 | 2.35 | 0.074 | 3 |
| Welland Flair Specimen 2 | 2.42 | | | |
| Product A Specimen 1 | 1.60 | 1.59 | 0.005 | 0 |
| Product A Specimen 2 | 1.59 | | | |
| Product B Specimen 1 | 1.62 | 1.64 | 0.027 | 2 |
| Product B Specimen 2 | 1.67 | | | |
| Product C Specimen 1 | 1.494 | 1.45 | 0.05 | 3 |
| Product C Specimen 2 | 1.399 | | | |
| Product D Specimen 1 | 1.11 | 0.95 | 0.164 | 17 |
| Product D Specimen 2 | 0.78 | | | |
| Product E Specimen | 2.09 | 2.09 | — | — |
| Product F Specimen | 2.17 | 2.17 | — | — |

As it may be derived from table 1 above, all of the tested products and prototypes have an average peak compression load, i.e. an axial compression resistance of between more than 12 Newtons to more than 50 Newtons corresponding to the products ranging from being relatively compressible, but

TABLE 1

| Test Specimen Product | Load [N] 1 mm Compression | Load [N] 2 mm Compression | Load [N] 3 mm Compression (peak load) | Average peak compression load [N] | Standard deviation | Standard deviation [%] |
|---|---|---|---|---|---|---|
| B. Braun Softima Specimens 1 & 2 | 8.353 | 33.453 | 54.046 | 55.50 | 1.45 | 3 |
| | 5.440 | 27.280 | 56.949 | | | |
| Coloplast SenSura Convex Light Specimens 1 & 2 | 4.683 | 9.530 | 13.265 | 12.68 | 0.58 | 5 |
| | 3.402 | 8.351 | 12.100 | | | |
| Convatec Esteem Specimens 1 & 2 | 10.430 | 33.019 | 52.841 | 54.93 | 2.08 | 4 |
| | 15.991 | 37.637 | 57.010 | | | |
| Dansac Nova Specimen 1 &2 | 7.115 | 17.336 | 21.607 | 21.52 | 0.09 | 0 |
| | 5.131 | 15.667 | 21.436 | | | |
| Hollister Moderma Flex Specimen 1 *) Max compr. load of equipment reached, specimen 2 not tested | 10.411 | 51.236 | 51.236 | *) | — | — |
| Salts Confidence Specimens 1 & 2 | 3.777 | 24.023 | 43.379 | 48.73 | 5.35 | 11 |
| | 15.996 | 38.172 | 54.084 | | | |
| Welland Flair Specimens 1 & 2 | 8.854 | 33.570 | 49.451 | 47.60 | 1.85 | 4 |
| | 9.018 | 32.508 | 45.747 | | | |
| Prod A Specimen 1 | 5.556 | 14.993 | 23.365 | 23.59 | 0.23 | 1 |
| Prod A Specimen 2 | 5.579 | 15.267 | 23.820 | | | |
| Prod B Specimen 1 | 4.142 | 13.688 | 20.688 | 21.20 | 0.52 | 2 |
| Prod B Specimen 2 | 6.185 | 15.159 | 21.720 | | | |
| Prod C Specimen 1 | 8.748 | 37.303 | 64.476 | 57.19 | 7.29 | 13 |
| Prod C Specimen 2 | 1.709 | 22.879 | 49.898 | | | |
| Prod D Specimen 1 | 3.851 | 9.212 | 13.387 | 13.43 | 0.04 | 0 |
| Prod D Specimen 2 | 3.159 | 8.974 | 13.472 | | | |
| Prod E Specimen | 2.105 | 9.343 | 15.642 | 15.64 | — | — |
| Prod F Specimen | 4.812 | 11.239 | 16.741 | 16.74 | — | — | still able to maintain a necessary peristomal pressure, to very rigid and practically inflexible in the axial direction.

Table 2 shows the average bending load, i.e. the resistance to bending of the products and prototypes. As seen in the table, all of the applicant's prototypes exhibit an average bending load below 2.25 Newton meaning that the prototypes are relatively flexible.

Some bendability resistance may be needed to avoid collapse of the peristomal skin area. Thereby, the bendability resistance preferably ranges between 0.8 N and 2.25 N.

Figure 27:
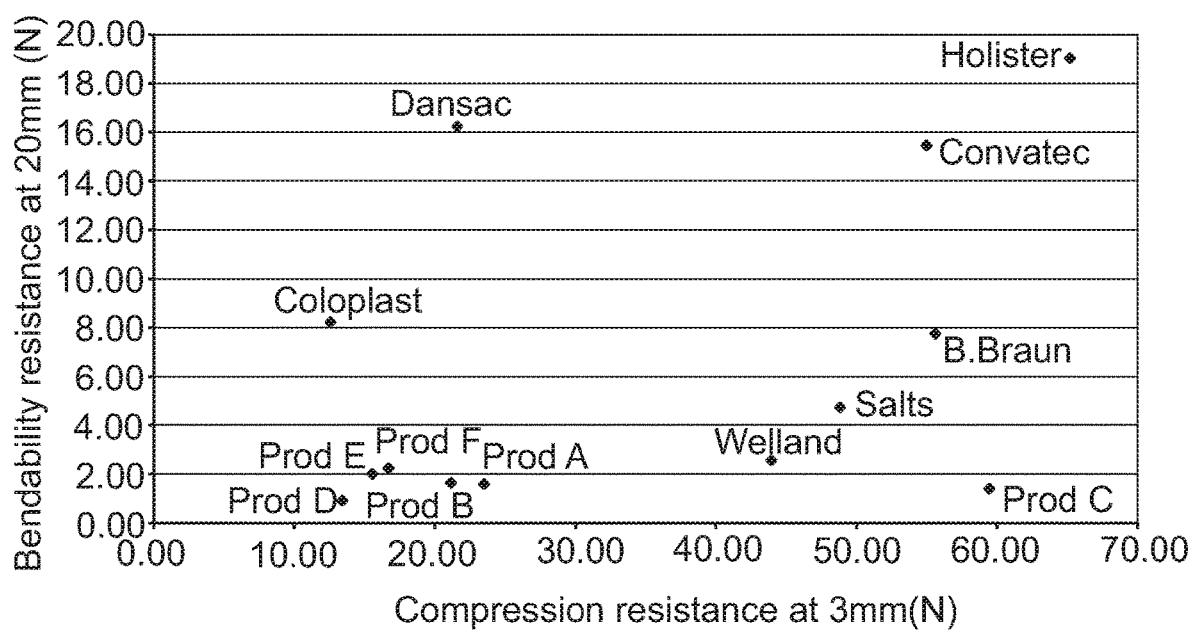
FIG. 27 is a graphic illustration plotting the measured bendability resistance and axial compression resistance of prior art devices and devices according to the invention.

When conjoining the values of tables 1 and 2 as expressed in FIG. 27 (and schematically indicated in FIG. 8), it is clear that the new technology according to the invention comprises the only product types that offer a comfortable level of bending resistance and security against peristomal collapse while simultaneously maintaining the necessary peristomal pressure to let the stoma protrude and reducing the risk of pressure ulcers significantly. In other words, in the present application it is realized that the prior art convex ostomy devices exert an unnecessary high pressure to the peristomal skin in order to achieve the beneficial effects of such convex devices namely to ensure that the stoma protrudes correctly and sufficiently into the collecting bag to prevent stomal output from leaking under the base plate as previously discussed. With the base plate according to the present invention, the same benefits are achieved only with a lower peristomal skin pressure reducing the risk of pressure ulcers.

Moreover, it is also realized by the present invention that the base plate does not need to have a high bending resistance, i.e. be very stiff, to maintain the necessary pressure on the peristomal skin. Indeed, another significant benefit of this invention is therefore also that a more skin friendly and less aggressive adhesive may be used to secure the convex appliance to the user's body than with the prior art convex devices. When applying the much more flexible base plate according to the invention on the skin, less adhesive force is required to make it stay in place because according to the invention the skin may now follow the user's body movements. This is contrary to the prior art products where the beneficial effects of the convex products are achieved by the high stiffness of the products forcing the skin to avoid collapse, but simultaneously compromising the product's ability to follow body movements and thus compromising the flexibility of the product. As less adhesive force is required to secure the base plate of the invention to the skin, it means that the adhesive may be more skin friendly because a weaker adhesive will, among other effects, result in less skin cell stripping upon removal of the product from the skin.

A particular advantage of the products of the invention is that with a base plate according to the various possible embodiments of the present invention having a bending resistance of 2.25 N or less when the product is bent 20 mm and an axial compression resistance of more than 10 N at 3 mm compression, products are achieved that will stay on the body for an increased time of wear because of the ability to better follow the body movements. The products are changed less often due to leakage. And when leakage occurs, the area of the adhesive affected is remarkably less. On top of these hard-core features, the users felt more free and comfortable with the flexible products.

It will be appreciated that individual user needs may determine how a product is designed according to the many possible combinations of the present invention. One user may need a product with a relatively high axial compression resistance while another user may need a product with a relatively moderate axial compression. With the present invention, products are obtained that provide these possibilities without compromising the comfort of a flexible, yet secure product.

We claim:

1. A convex shell for use in a base plate of an ostomy appliance, the
convex shell comprising:
an annular ring defined by an outer edge in a first plane and an inner edge in a second plane, the inner edge defining a through-going hole having a center axis, the first plane axially offset along the center axis from the second plane, the annular ring including:
an outer planer surface extending radially inward from the outer edge in the first plane;
an inner planer surface extending radially outward from the inner edge in the second plane;
an intermediate surface extending radially inward from the outer planer surface to the inner planer surface; and
a plurality of grooves, with each groove extending radially on a line aligned with a center of the through-going hole and formed in the outer planer surface and the inner planer surface and the intermediate surface, the plurality of grooves alters the flexibility of the annular ring as a first portion of the annular ring is folded around a folding axis toward a second portion of the annular ring.

2. The convex shell according to claim 1, wherein the plurality of grooves includes six grooves, wherein each of the six grooves includes a first groove wall and a second groove wall defining a folding angle α.

3. The convex shell according to claim 2, wherein the first groove wall and the second groove wall are made from different materials having different compression characteristics.

4. The convex shell according to claim 2, wherein not all of the six grooves define the same folding angle α so that the convex shell can provide flexibility in further intervals.

5. The convex shell according to claim 1, wherein the plurality of grooves is placed on a first side facing the user, when the product is in use.

6. The convex shell according to claim 1, wherein the plurality of grooves is placed on a second side facing away from the user, when the product is in use.

7. A convex shell for use in a base plate of an ostomy appliance, the
convex shell comprising:
an annular ring defined by an outer edge in a first plane and an inner edge in a second plane, the inner edge defining a through-going hole having a center axis, the first plane being axially offset along the center axis from the second plane, the annular ring including at least one groove extending radially on a line aligned with a center of the through-going hole and formed in the first plane and the second plane, the at least one groove adapted to alter the flexibility of the annular ring when the annular ring is folded around a folding axis.

8. The convex shell according to claim 7, wherein the at least one groove extends along the folding axis.

9. The convex shell according to claim 7, wherein a first resulting reactive force of the convex shell when an angle around the folding axis between a first portion of the annular ring and a second portion of the annular ring is between 180 and 90 degrees and is less than a second resulting reactive force of the convex shell when the angle around the folding axis between the first portion of the annular ring and the second portion of the annular ring is between 90 and 20 degrees.

10. The convex shell according to claim 7, wherein the at least one groove includes two opposite contact surfaces which move toward each other as a first portion of the annular ring is folded around the folding axis toward a second portion of the annular ring.

11. The convex shell according to claim 10, wherein a first force required to fold the first portion of the annular ring toward the second portion of the annular ring when the two opposite contact surfaces are not in contact with each other is less than a second force required to further fold the first portion of the annular ring toward the second portion of the annular ring when the two opposite contact surfaces are in contact with each other.

12. The convex shell according to claim 7, wherein the at least one groove is placed on a first side facing the user, when the product is in use.

13. The convex shell according to claim 7, wherein the at least one groove is placed on a second side facing away from the user, when the product is in use.

14. The convex shell according to claim 7, wherein the at least one groove includes a plurality of grooves formed across the annular ring.

15. The convex shell according to claim 14, wherein the plurality of grooves is placed on a first side facing the user and on the second side facing away from the user, when the product is in use.

16. The convex shell according to claim 14, wherein each groove of the plurality of grooves includes two opposite contact surfaces which move toward each other as the first portion of the annular ring is folded around the folding axis toward the second portion of the annular ring, the two opposite contact surfaces for each groove of the plurality of grooves contacting each other when the convex shell is folded to a predetermined angle around the folding axis.

17. The convex shell according to claim 16, wherein the predetermined angle is not the same for each groove of the plurality of grooves.

18. The convex shell according to claim 16, wherein each groove of the plurality of grooves extends in a radial direction.

19. The convex shell according to claim 16, wherein the plurality of grooves includes a plurality of first grooves and a plurality of second grooves, the plurality of first grooves extending in a first direction across the annular ring, and the plurality of second grooves extending in a second direction across the annular ring, the first direction transverse to the second direction.

20. The convex shell according to claim 16, wherein at least some of the plurality of grooves extend to the inner edge of the annular ring, at least some of the plurality of grooves extend to the outer edge of the annular ring.

* * * * *